US011253381B2

(12) United States Patent
Doyle

(10) Patent No.: US 11,253,381 B2
(45) Date of Patent: Feb. 22, 2022

(54) HEAD SUPPORT SYSTEMS AND METHODS FOR USE

(71) Applicant: ENHANCE TECHNOLOGIES, LLC, San Diego, CA (US)

(72) Inventor: Mark C. Doyle, Del Mar, CA (US)

(73) Assignee: Enhance Technologies, LLC, San Diego, CA (US)

( * ) Notice: Subject to any disclaimer, the term of this patent is extended or adjusted under 35 U.S.C. 154(b) by 511 days.

(21) Appl. No.: 16/019,455

(22) Filed: Jun. 26, 2018

(65) Prior Publication Data

US 2018/0303650 A1    Oct. 25, 2018

Related U.S. Application Data

(63) Continuation of application No. PCT/US2016/069032, filed on Dec. 28, 2016.
(Continued)

(51) Int. Cl.
*A61F 5/01* (2006.01)
*B25J 9/10* (2006.01)
(Continued)

(52) U.S. Cl.
CPC ........ *A61F 5/0102* (2013.01); *A41D 13/0007* (2013.01); *A41D 13/0568* (2013.01);
(Continued)

(58) Field of Classification Search
CPC .. A61F 5/05883; A61F 5/05891; A61F 5/055; A61F 5/30; A61F 5/0102;
(Continued)

(56) References Cited

U.S. PATENT DOCUMENTS 4,453,271 A * 6/1984 Donzis ............... A41D 13/0153
2/2.5
5,242,377 A 9/1993 Boughner et al.
(Continued)

FOREIGN PATENT DOCUMENTS

CA          2467787 A1   11/2005
IT    102011901935708 A1   10/2012
(Continued)

OTHER PUBLICATIONS

Park, Tae Wook, Korean Intellectual Property Office, International Search Report and Written Opinion for related International Application No. PCT/US2016/069032, dated Apr. 20, 2017, 18 pages.
(Continued)

*Primary Examiner* — Camtu T Nguyen
(74) *Attorney, Agent, or Firm* — William A. English; Vista IP Law Group LLP

(57) ABSTRACT

Systems and methods are provided for supporting a head of a user, e.g., while the user inclines their head downward, leans forward, and the like, for extended periods of time. In an exemplary embodiment, a harness is provided that is configured to be worn on a body of a user, the harness including a shoulder harness configured to be worn over or around one or both shoulders of the user, and a head support. The head support may include a support bracket including a first end mounted to the harness, and a rest member coupled to a second end of the support bracket such that the rest member extends across a forehead of the user and/or at least partially around the user's head when the harness is worn for supporting the user's forehead.

12 Claims, 30 Drawing Sheets

Related U.S. Application Data

(60) Provisional application No. 62/271,957, filed on Dec. 28, 2015.

(51) Int. Cl.
| | |
|---|---|
| *B25J 9/00* | (2006.01) |
| *A61B 34/00* | (2016.01) |
| *A41D 13/00* | (2006.01) |
| *A41D 13/05* | (2006.01) |
| *A61F 5/30* | (2006.01) |
| *A61F 9/06* | (2006.01) |
| *A61B 90/50* | (2016.01) |

(52) U.S. Cl.
CPC ............... *A61B 34/70* (2016.02); *A61F 5/30* (2013.01); *A61F 9/06* (2013.01); *B25J 9/0006* (2013.01); *B25J 9/1045* (2013.01); *A61B 2090/502* (2016.02); *A61F 2005/0146* (2013.01)

(58) Field of Classification Search
CPC .. A61F 9/06; A61F 9/061; A61F 9/062; A61F 9/064; A61F 9/065; A61F 9/067; A61F 9/068; A61B 2090/502; A61B 2090/504; A61B 2090/5025; A42B 3/0473; A42B 3/228; A61H 1/0292; A61H 1/0296; A61H 3/00; A61H 2003/007; A61H 3/008; A61H 2201/1604; A61H 2201/1607; A61H 2201/1609; A61H 2201/1611; A61H 2201/1614; A61H 2201/1616; A61H 2201/1623; A61H 2201/1626; A61H 2201/1652; A61H 2205/02; A61H 2205/021; A61H 2205/04; A61H 2205/081
See application file for complete search history.

(56) References Cited

U.S. PATENT DOCUMENTS

| | | | |
|---|---|---|---|
| 5,306,232 A | | 4/1994 | Whitmyer |
| 5,314,404 A | * | 5/1994 | Boughner ............... A61F 5/055 128/876 |
| 5,371,905 A | * | 12/1994 | Keim ................... A42B 3/0473 2/413 |
| 6,306,232 B1 | | 10/2001 | Khandhadia et al. |
| 8,721,577 B1 | * | 5/2014 | Perry ..................... A61F 5/026 602/19 |
| 9,603,405 B2 | * | 3/2017 | Blecherman ......... A42B 3/0473 |
| 2004/0068779 A1 | * | 4/2004 | Duffy ................... A42B 3/0473 2/422 |
| 2008/0060102 A1 | * | 3/2008 | Matthews ............... A61F 9/061 2/8.2 |
| 2010/0286581 A1 | | 11/2010 | Hipp et al. |
| 2011/0240042 A1 | | 10/2011 | Cooke et al. |
| 2012/0136292 A1 | | 5/2012 | Pepin et al. |
| 2017/0245576 A1 | * | 8/2017 | Hetzler ................ A42B 3/0406 |

FOREIGN PATENT DOCUMENTS

| | | |
|---|---|---|
| JP | 2000325377 A | 11/2000 |
| WO | 2014093408 A2 | 6/2014 |

OTHER PUBLICATIONS

Barnas, Christoph, European Search Report for corresponding European Application No. 16882612.1, dated Mar. 25, 2020, 7 pages.

Park, Tae Wook, Korean Intellectual Property Office, International Search Report and Written Opinion for corresponding International Application No. PCT/US2016/069032, dated Apr. 20, 2017, 18 pages.

Tanigawa, Keisuke, Aoyama International Patent Office, Office Action for corresponding Japanese Patent Application No. 2018-553060, dated Nov. 19, 2020, 10 pages.

Barnas, Christoph, European Patent Office, Supplementary Search Report and Opinion for corresponding European Patent Application No. 16882612.1, dated Mar. 17, 2020, 6 pages.

* cited by examiner

HEAD SUPPORT SYSTEMS AND METHODS FOR USE

RELATED APPLICATION DATA

The present application is a continuation of co-pending International Application No. PCT/US2016/069032, filed Dec. 28, 2016, which claims benefit of provisional application Ser. No. 62/271,957, filed Dec. 28, 2015, the entire disclosures of which are expressly incorporated by reference herein.

FIELD OF THE INVENTION

The present invention relates to systems, devices, and methods for supporting a user's body, e.g., the user's head and/or arms.

BACKGROUND

Many tasks require that people work with their heads inclined downward and/or leaning forward, in order to properly visualize their work. Examples include surgery and welding. Extended periods of working with the head inclined downward (declined) can result in detrimental effects on the structures of the neck, which bears the weight of the worker's head, such as fatigue, discomfort, and injury.

FIGS. 1A and 1B show a User U, in a typical work position, optionally wearing an arm support system 10, which may adaptively support the left arm LA and right arm RA, e.g., through the use of interchangeable cassettes 12 and armrests 14. All, or a portion of, the weight of the user's arms is thereby transferred from the muscles of the shoulder and upper back to the torso of the user. As shown in FIG. 1B, the User U's head H is declined approximately along path P1, creating strain on the structures of the user's neck N as it bears the weight of the user's head H. Optional arm support system 10 might support the user's arms (RA and LA), but cannot aid in supporting the user's head H, and thus cannot relieve strain on the user's neck N.

U.S. Pat. No. 5,242,377 discloses a medical restraint device intended to maintain the head of a person with neck dysfunction in a desired head position, while U.S. Pat. No. 5,306,232 discloses a head alignment system for a person having reduced musculature or loss of muscle control to maintain the person's head in a generally upright position. Thus, these devices are intended to restrain the user's head rather than support the head during normal activities.

Therefore, devices, systems, and methods for supporting a user's head while allowing the user to move their head freely while performing tasks, e.g., to prevent or reduce fatigue, would be useful.

SUMMARY

The present invention is directed to systems, devices, and methods for supporting a user's body, e.g., the user's head and/or arms.

In accordance with an exemplary embodiment, a system is provided for supporting a head of a user that includes a harness configured to be worn on a body of a user, the harness including a shoulder harness configured to be worn over or around one or both shoulders of the user, and a head support comprising a support bracket comprising a first end mounted to the harness, and a rest member coupled to a second end of the support bracket such that the rest member extends across a forehead of the user when the harness is worn for supporting the user's forehead.

In accordance with another embodiment, a system is provided for supporting a head of a user that includes a harness configured to be worn on a body of a user, the harness including a shoulder harness configured to be worn over or around one or both shoulders of the user; and a head support comprising a support bracket comprising a first end mounted to the harness at a location such that the support bracket is positioned behind or otherwise adjacent the head of a user wearing the harness, and a rest member coupled to a second end of the support bracket such that the rest member extends around the head of the user to contact the user's forehead when the harness is worn.

In accordance with yet another embodiment, a system is provided for supporting a head of a user that includes a harness configured to be worn on a body of a user, the harness comprising a shoulder harness configured to be worn over or around one or both shoulders of the user, and a head support on the harness. Optionally, the system may also include an arm support coupled to the harness configured to support an arm of the user, the arm support configured to accommodate movement of the arm while following the movement without substantially interfering with the movement of the user's arm; and one or more compensation elements mounted on the arm support to at least partially offset a gravitational force acting on the user's arm as the user moves and the arm bracket follows the movement of the user's arm. The one or more compensation elements may be configured to provide a force profile that varies the offset force based on an orientation of the arm support.

In accordance with still another embodiment, a system is provided for supporting a head of a user that includes a harness configured to be worn on a body of a user, the harness including a shoulder harness configured to be worn over or around one or both shoulders of the user, and a head support. The head support may include a support bracket comprising a first end mounted to the harness at a location such that a second end of the support bracket is positioned adjacent the head of a user wearing the harness; one or more pulleys carried on the second end of the support bracket; a rest member sized to extend at least partially around the head of the user to contact the user's forehead when the harness is worn; and an elongate cord coupled to the rest member and extending partially around the one or more pulleys to accommodate rotation of the user's head, the cord comprising an elastic structure to allow the user to decline the head and provide a counterbalancing force to at least partially support the weight of the head.

In accordance with yet another embodiment, a system is provided for supporting a head of a user that includes a harness configured to be worn on a body of a user, the harness including a shoulder harness configured to be worn over or around one or both shoulders of the user; a head support comprising a support bracket comprising a first end mounted to the harness at a location such that a second end of the support bracket is positioned adjacent a back of the head of a user wearing the harness; headgear configured to be worn on the user's head, the headgear comprising a band sized to extend around the back of the head of the user; and an elongate cord coupled between the second end of the support bracket and the headgear, the cord comprising an elastic structure to allow the user to decline the head and provide a counterbalancing force to at least partially support the weight of the head.

In accordance with another embodiment, a method is provided for supporting a user's head that includes wearing a harness on a user's body carrying a head support comprising a support bracket comprising a first end mounted to the harness at a location such that a second end of the support bracket is positioned adjacent a back of a head of the user; positioning a rest member coupled to the support bracket such that the rest member extends at least partially around the head of the user to contact the user's forehead; and performing one or more tasks involving the head declining and rotating, the rest member accommodating rotation of the head and providing a counterbalancing force to at least partially offset the weight of the head when the head is declined.

Other aspects and features of the present invention will become apparent from consideration of the following description taken in conjunction with the accompanying drawings.

BRIEF DESCRIPTION OF THE DRAWINGS

The present invention is best understood from the following detailed description when read in conjunction with the accompanying drawings. It will be appreciated that the exemplary devices shown in the drawings are not necessarily drawn to scale, with emphasis instead being placed on illustrating the various aspects and features of the illustrated embodiments.

DETAILED DESCRIPTION OF THE EXEMPLARY EMBODIMENTS

Turning to the drawings, FIGS. 2A-2D show a first exemplary embodiment of a support system 50 worn by a user U. Generally, the system 50 includes a harness and a head support, and, optionally may include an arm support mechanism for supporting one or both of the user's arms (two arm supports shown supporting the user's right arm and left arm). The harness generally may include one or more of an attachment band configured to be worn around the user's torso, e.g., chest, waist, and/or hips, a shoulder harness configured to be worn over and/or around the user's shoulders, and/or one or more vertical supports, e.g., extending between the attachment band and the shoulder harness (all not shown for clarity), e.g., similar to the support systems disclosed in U.S. Publication Nos. 2012/0184880, 2014/0033391, 2014/0158839, and 2015/0316204, the entire disclosures of which are expressly incorporated by reference herein. In addition, the harness may include a shoulder bracket and/or frame with a fixed end disposed above or adjacent to the user's shoulder to which other components of the system 10 may be coupled, e.g., to provide the arm support, which pivots about one or more axes relative to the shoulder bracket, similar to the systems in these publications. The systems herein may also include additional components similar to those disclosed in these publications, such as a cassette 12 for providing a desired and/or variable offsetting force and armrest 14, as desired.

Figure 1A:
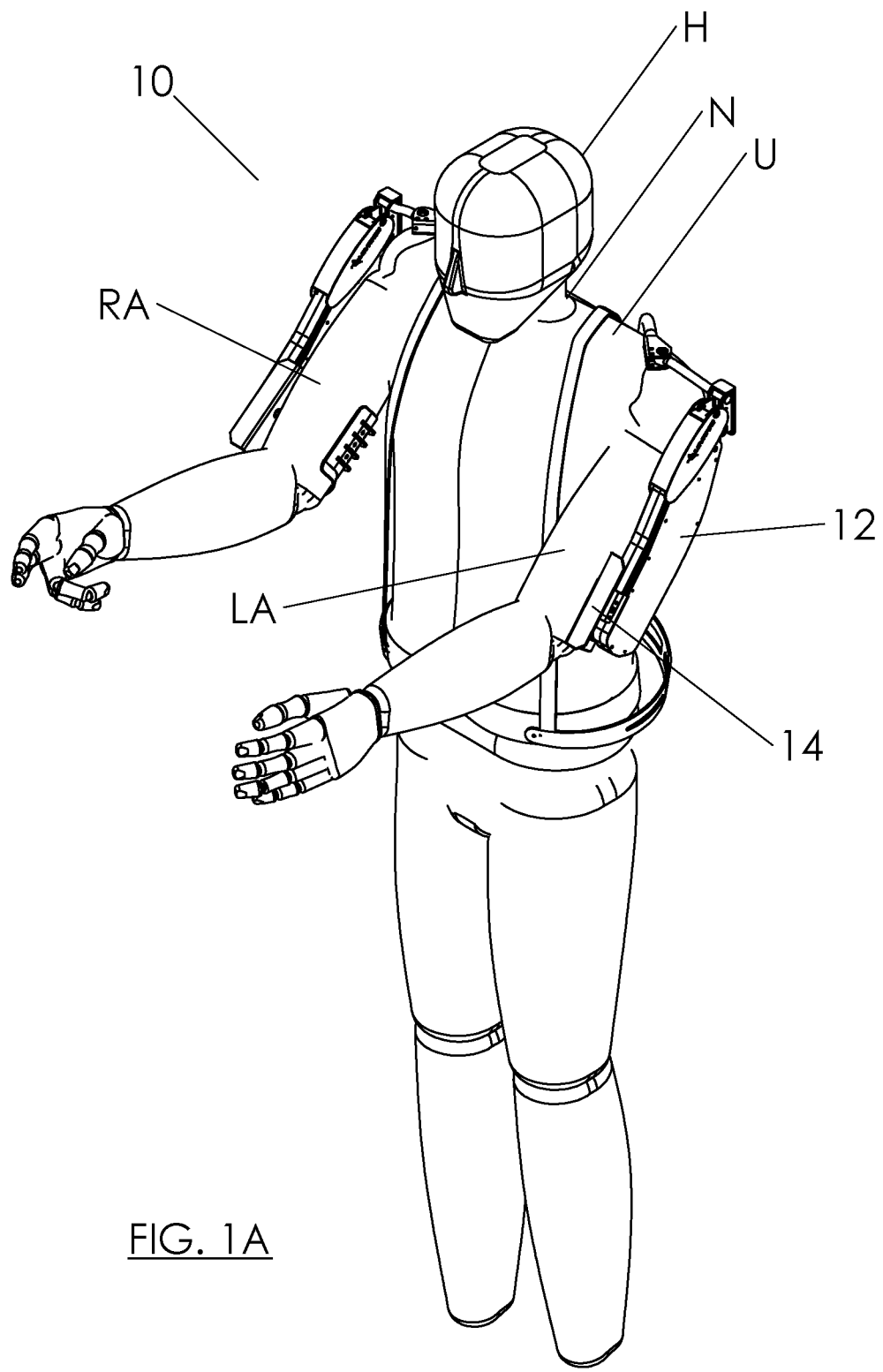
FIGS. 1A and 1B are perspective views of an arm support system worn by a user to support the user's arms, showing the user's head raised and lowered, respectively.
Figure 1B:
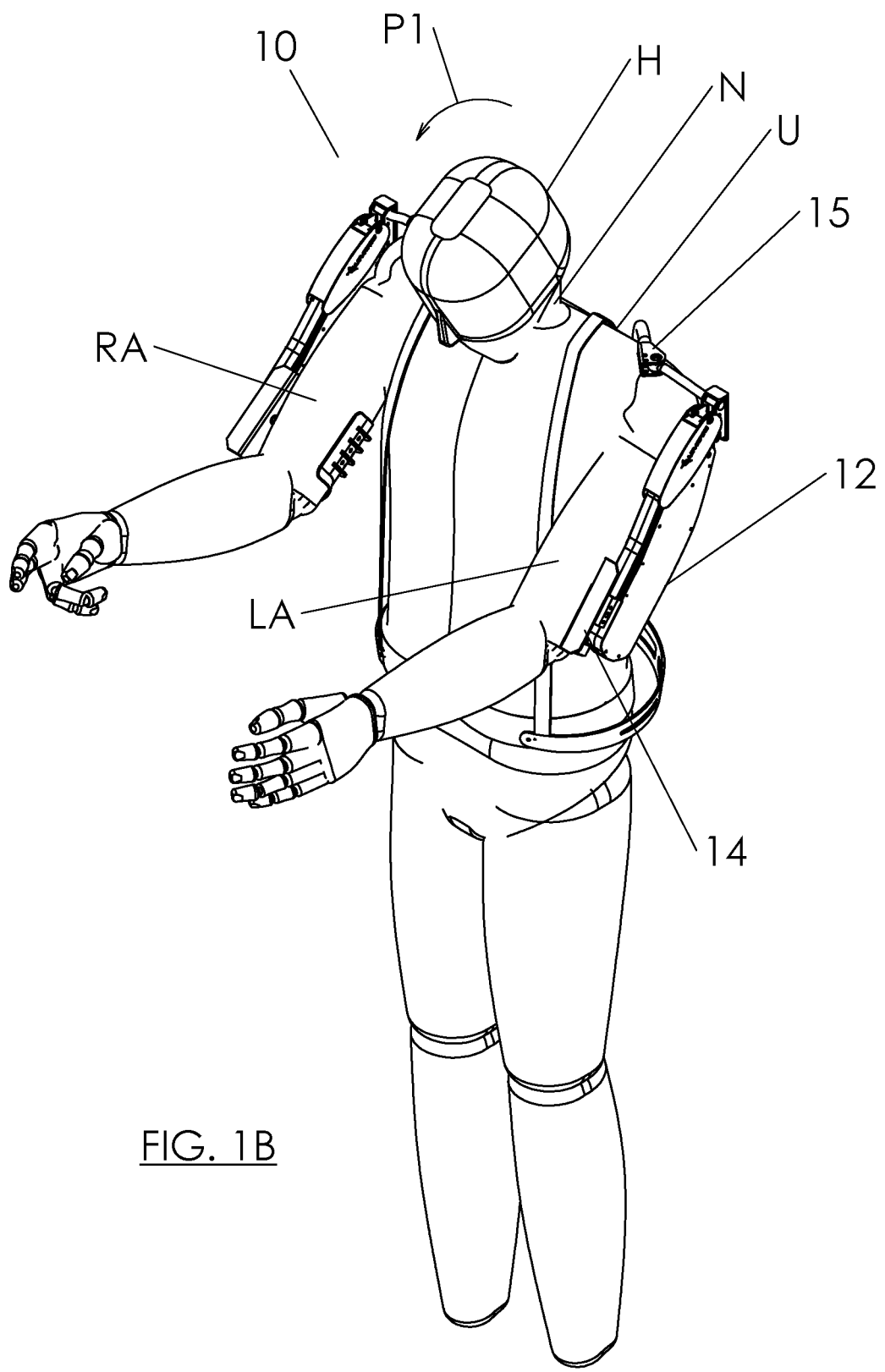
Figure 2A:
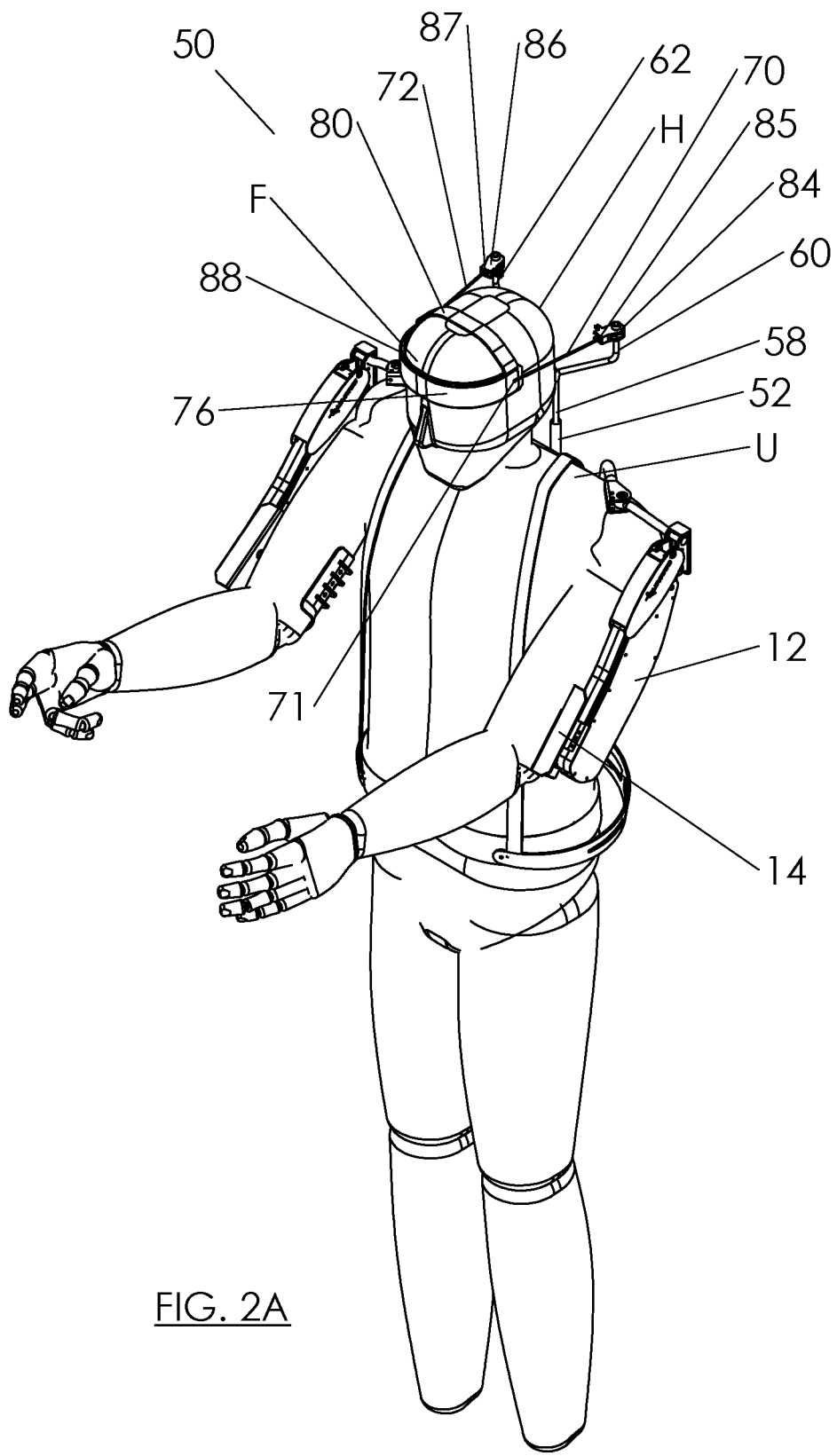
FIGS. 2A-2D are perspective views of an exemplary embodiment of a support system worn by a user that supports the user's head, showing the head in various positions.
Figure 2B:
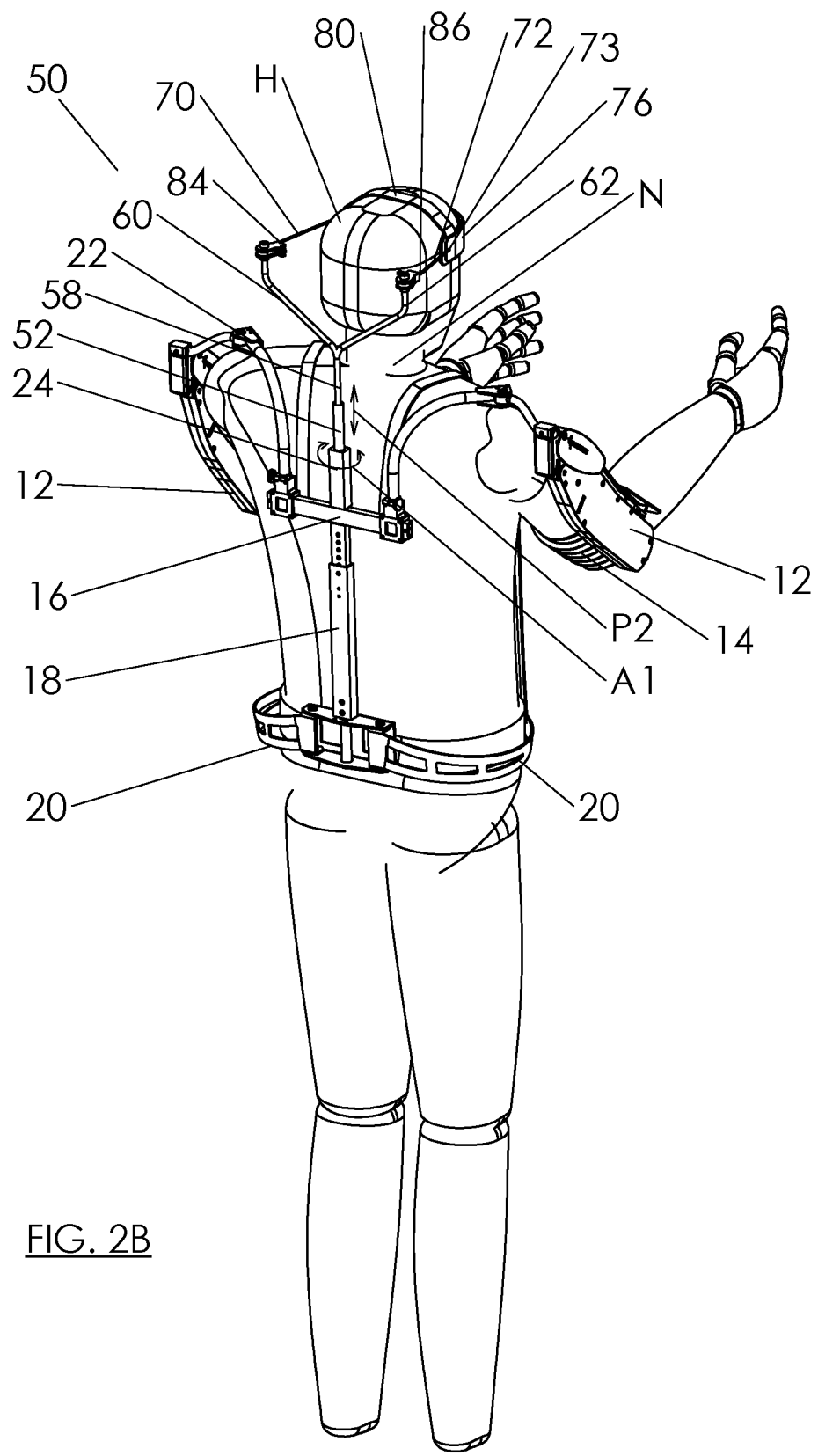

As shown in FIG. 2A, User U is shown wearing an arm support system 50 that includes components that also serve to support the user U's head H, which is shown level (referred to herein as "non-declined"). A forehead band 76 is located on the user's forehead F. Optional pad 88 may be positioned between the forehead band 76 and the user's forehead F. Forehead band 76 may be flexible, semi-flexible, or rigid. Optional crown band 80, including one or more straps arranged to extend at least partially over the top of the user's head H, may assist in locating forehead band 76 on forehead F. Optionally, a strap may be provided that extends around the back of the user's head (not shown), e.g., to enhance keeping the band 76 in place. Elastic elements, elongate elastic bands 70 and 72, are joined at opposite ends to the forehead band 76 at locations 71 and 73 (73 is shown in FIG. 2B), and to buckles 84 and 86, respectively. Buckles 84 and 86, which may provide an adjustment function for the length of elastic elements 70 and 72, are in turn joined (optionally pivotally) to Y-frame bars 60 and 62, which are joined to Y-frame post 58, and ultimately to the frame at the back of the arm support system 50, as described below. Elastic elements 70 and 72 may be made from any known elastic material, such as latex rubber, silicone or polyurethane elastomer, or may be formed from commonly known spring structures, such as coil springs or constant force springs. In the non-declined position of the head H shown, little stress is experienced by the user's neck, and elastic bands 70 and 72 may be relatively un-tensioned.

FIG. 2B shows a rear view of the system 50 of FIG. 2A. Y-frame post 58, which supports and locates Y-frame bars 60 and 62, is joined to socket post 52. Socket post 52 is inserted into frame socket 24, and may be able to rotate relative to frame socket 24 approximately along arc A1, e.g., by the use of commonly known components such as bearings or bushings (not shown). Socket post 52 may also be adjustable vertically relative to frame socket 24, approximately along path P2, e.g., by the use of commonly known components such as clamps, screws, shaft collars, clips, or screws (not shown). Socket post 52 and attached Y-frame bars 60 and 62 may be removable from frame socket 24, for example, if the head support is not needed. Y-frame post 58 and Y-frame bars 60 and 62 may be rigid or flexible, or may be formable by bending in order to shape them as desired. For example, in the embodiment shown, both the Y-frame post 58 and both Y-frame bars 60, 62 are rigid with the elastic bands 70, 72 stretching elastically to allow the user's head H.

The Y-frame post 58 may be coupled to a frame of a harness, e.g., carrying an arm support system. For example, as shown in FIG. 2B, frame socket 24 is joined to frame T 16, which in turn connects to spine tube 18, which is joined to belt strut(s) 20. Frame socket 24, frame T 16, spine tube 18, and belt strut(s) 20 provide a substantially rigid structure by which loads such as the weight of the user's arms or head are transferred through flexible elements onto the user's torso and hips.

Figure 2C:
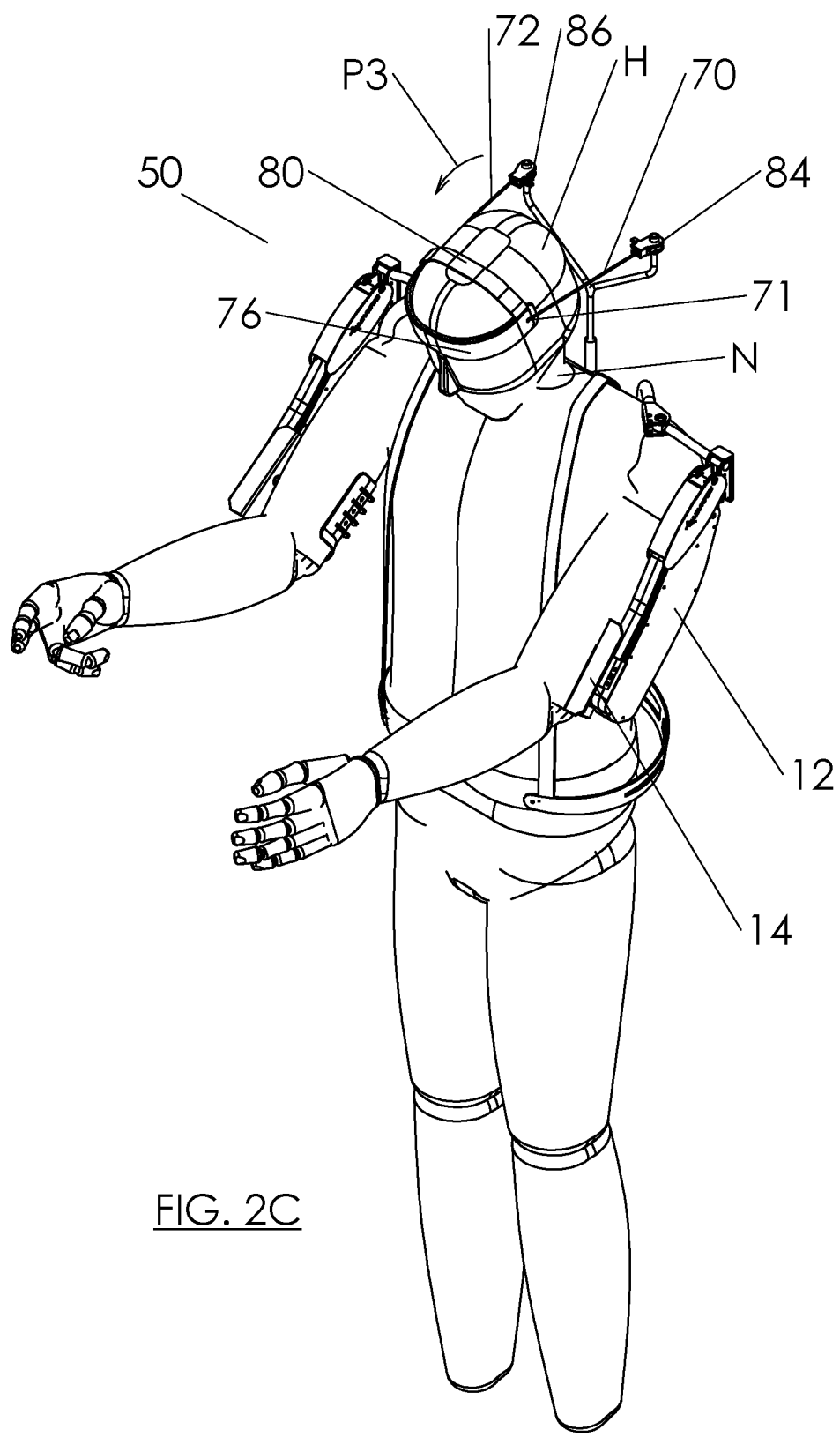

FIG. 2C shows the user U wearing the arm support system 50 of FIGS. 2A and 2B, with the user's head H bending forward at the neck (referred to herein as "declined") approximately along path P3. Elastic elements 70 and 72, in response, have extended and lengthened. In the case of elastic elements that conform approximately to Hooke's law, the force in the elastic elements will increase as they extend, creating an increasing counterbalancing force to support the user's head H. The amount of counterbalancing force at a given position may be selected by the user, for example, by selecting elastic elements with more or less spring rate, or by adjusting the length of the elastic elements with buckles 84 and 86. In the case of elastic elements that do not conform to Hooke's law, such as constant-force springs, the counterbalancing force will remain the same.

Figure 2D:
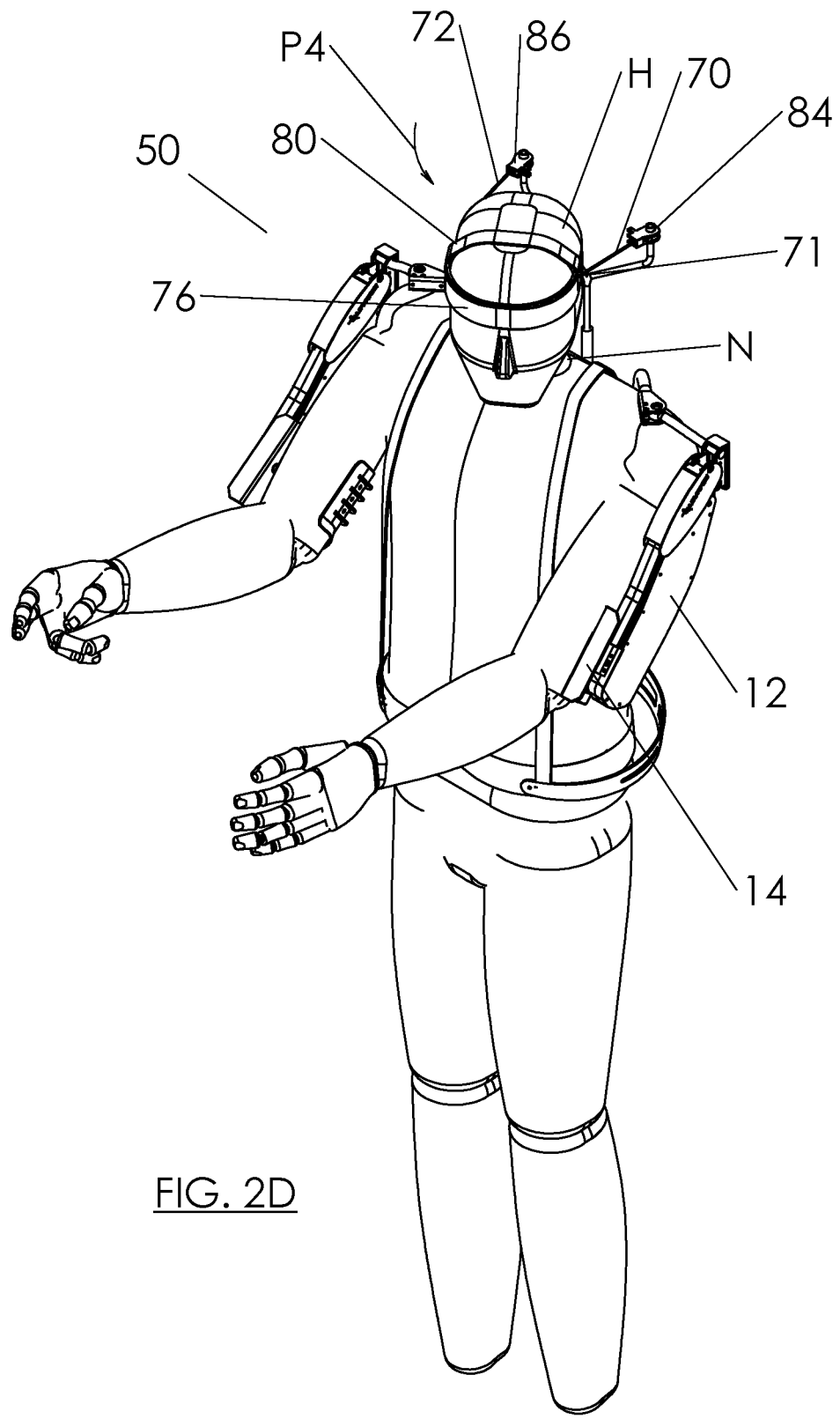

FIG. 2D shows the user U wearing the arm support system 50 of FIG. 2C, with the user's head declined and rotated to the left approximately along path P4. As user U rotates their head to one side, elastic elements 70 and 72 may extend or retract in response. Additionally, buckles 84 and 86 may pivot about the end of Y-frame bars 60 and 62 in response. Elastic element 72 may extend in response to the motion along path P4, while elastic element 70 may shorten, or remain the same length.

Figure 3A:
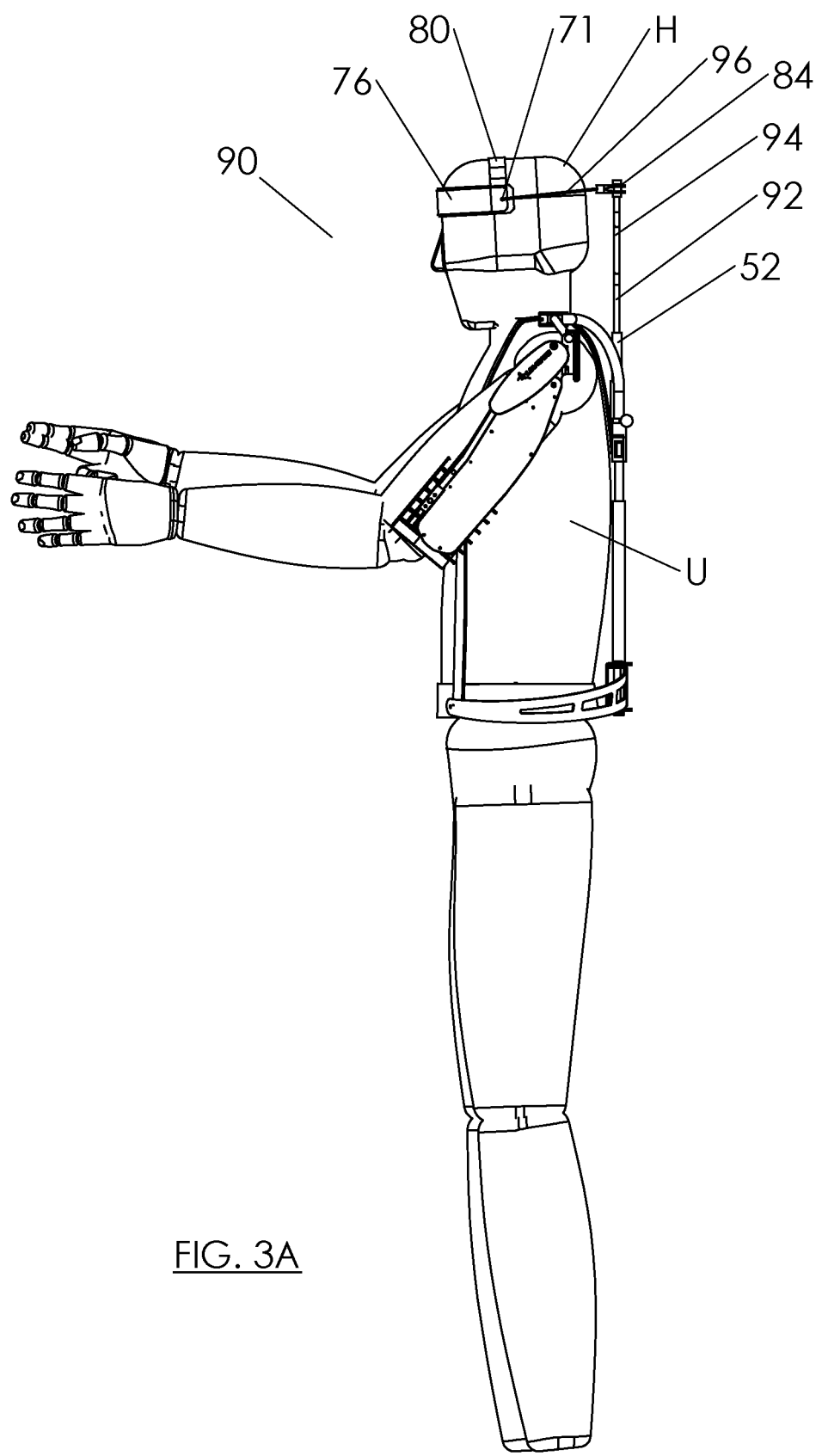
FIGS. 3A and 3B are side views of another embodiment of a support system supporting the head of a user with the head non-declined and declined, respectively.

Turning to FIG. 3A, another exemplary embodiment of an arm support system 90 is shown that is generally similar to the embodiment of FIGS. 2A-2D, showing the user U with head H non-declined and with the flexibility of the head support being provided by the Y-frame bars and post Unlike the previous embodiment, at least one of the Y-frame post 92 and Y-frame bar 94 is elastically deflectable in one or more directions to accommodate movement of the head H, while elongate elements 96 connecting the forehead band 76 to the Y-frame bar 94 are substantially inelastic. As shown in FIG. 3A, Y-frame post 92 and Y-frame bar 94 are un-deflected as the user works with their head H non-declined. Elongate elements 96, attached to Y-frame bar 94 by buckle 84, and attached to forehead band 76 at point 71, may be relatively inelastic elongate cords, cable, wires, and the like.

Figure 3B:
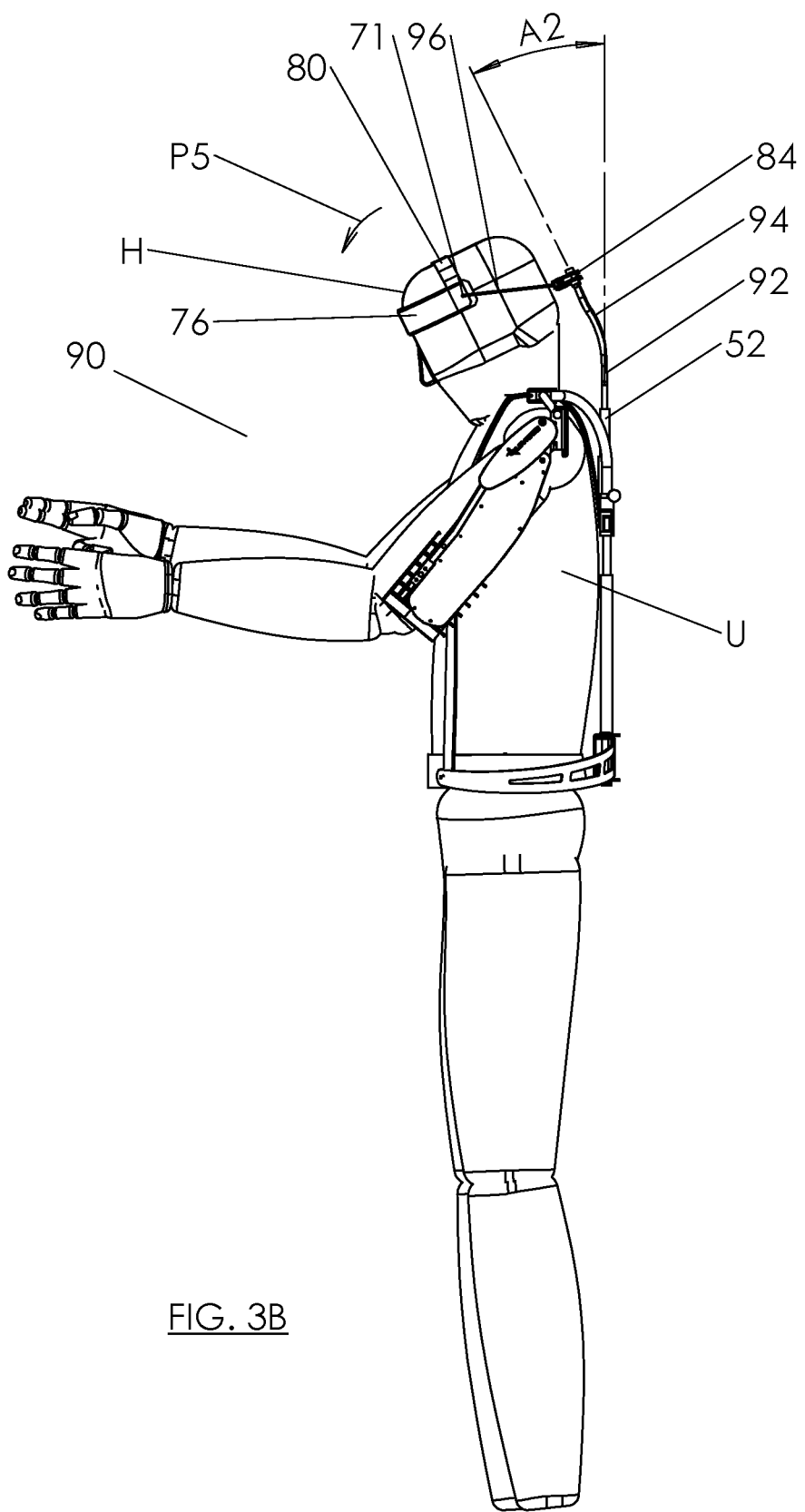

FIG. 3B shows the arm support system 90 with the user's head H declined, approximately along path P5. In response, Y-frame post 92 and Y-frame bar 94 are shown deflected, approximately along arc A2, and are providing a counterbalancing force on the user's head, e.g., acting as a leaf spring. Each elongate element 96 (inelastic) remains approximately the same length.

Figure 4A:
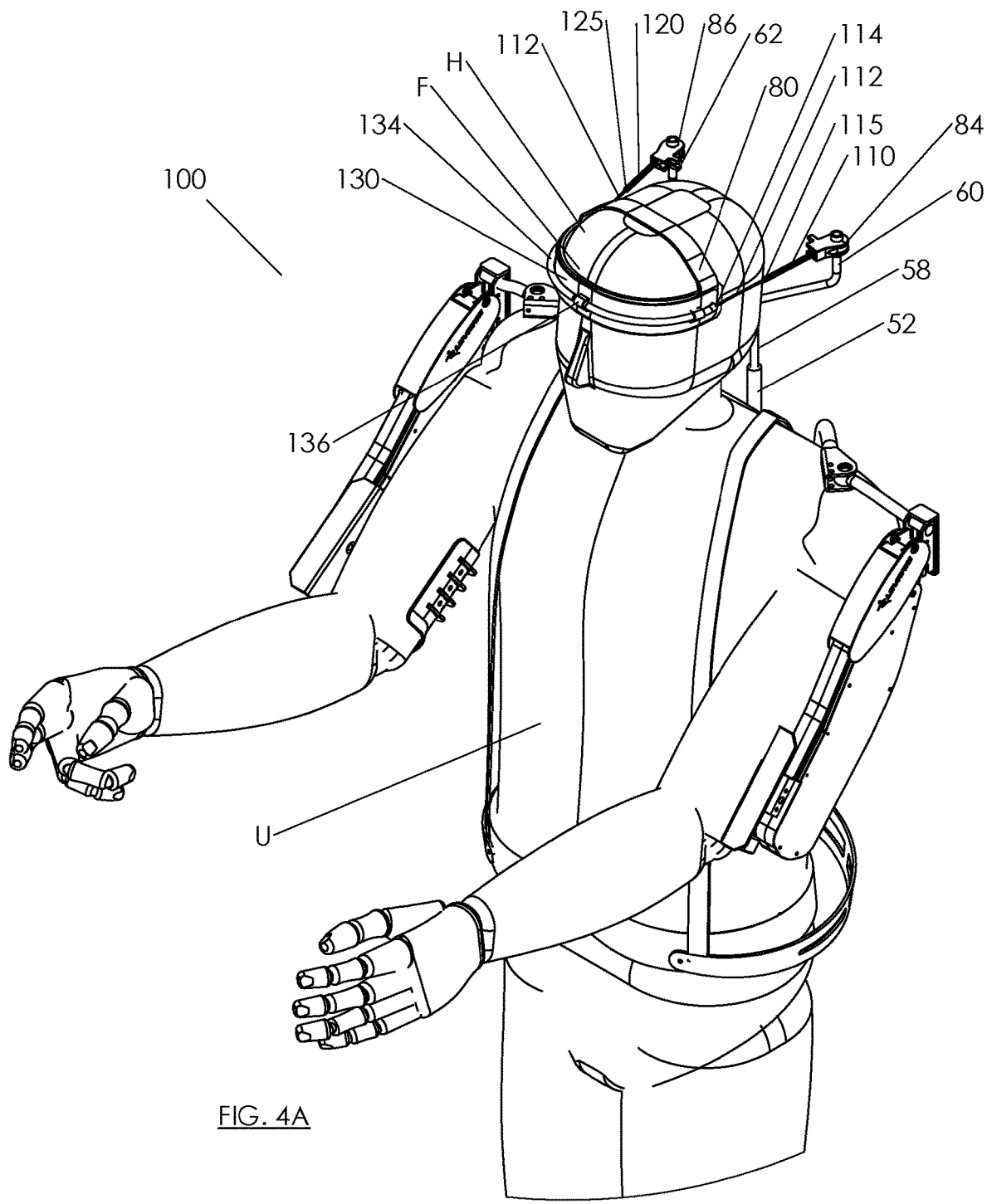
FIGS. 4A-4C are perspective views of yet another embodiment of a support system supporting the head of a user with the head non-declined, declined, and turned, respectively.

FIG. 4A shows another exemplary embodiment of an arm support system 100 with a head support system, which is a variant of the system 50 of FIGS. 2A-2D. Y-frame bars 60 and 62, Y-frame post 58, socket post 52, and buckles 84 and 86 are the same as in system 50. Forehead band 130, which may be flexible, semi-flexible, or rigid, is located on the user's forehead F. Crown band 80 assists in properly locating the forehead band 130. Optionally, a strap may be provided that extends around the back of the user's head (not shown), e.g., to enhance keeping the band 76 in place. A guide tube 134 is secured to the forehead band, for example, by guide tube clips 136 or other connectors (not shown). Guide tube 134 may be rigid or flexible, and may be made from, or lined with, a low friction material such as PTFE or Nylon. Guide tube 134 provides a track in which cord 112 may slide. Optionally, a lubricant (not shown) may be provided within the guide tube 134 to aid in smooth sliding motion of the cord 112 within the guide tube 134. Smooth sliding motion of the cord 112 within the guide tube 134 facilitates rotation of the head from side to side with minimal resistance.

The cord 112 may be coupled to the Y-frame bar 60, e.g., via one or more elastic elements. For example, both ends of the core 112 may be joined to separate elastic elements 110 at coupling 115. Elastic elements 110 are in turn joined to Y-frame bar 60 at buckle 84. The equivalent elastic element 120, joined to the other end of cord 112 at coupling 125, is joined to Y-frame bar 62 at buckle 86. With the user's head H non-declined, as shown, the elastic elements 110 and 120 are relatively un-tensioned. Alternatively, a single elastic element may be provided on one end of the (inelastic) cord and the other end of the cord may be connected directly to the buckle 86 or Y-frame bar 62.

Figure 4B:
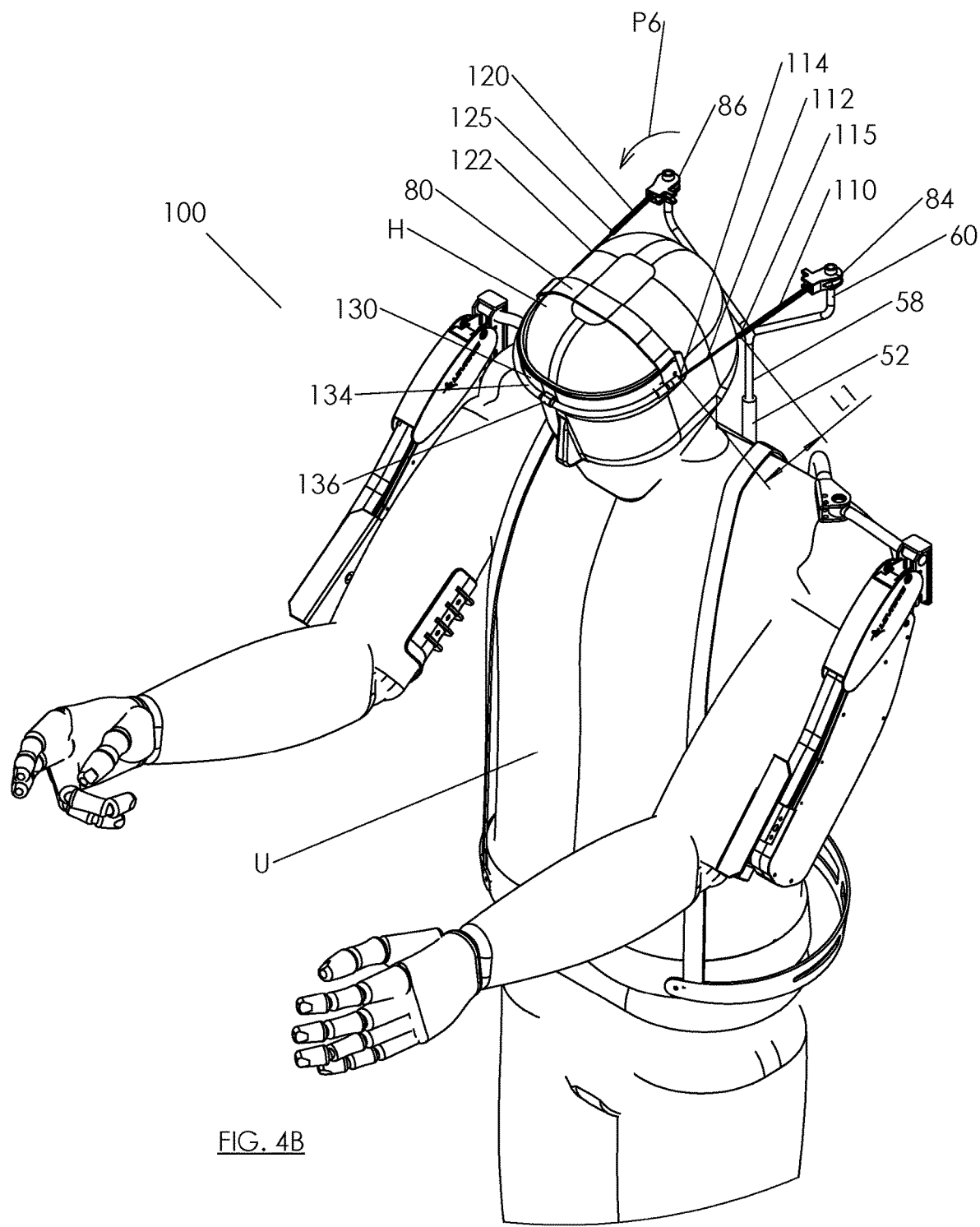

FIG. 4B shows the arm support system 100 of FIG. 4A with the user's head declined, approximately along path P6. As in FIG. 2C, elastic elements 110 and 120 have extended in response. In the case of elastic elements that conform approximately to Hooke's law, the force in the elastic elements will increase as they extend, creating an increasing counterbalancing force to support the user's head H. The amount of counterbalancing force at a given position may be selected by the user, for example, by selecting elastic elements with more or less spring rate, or by adjusting the length of the elastic elements with buckles 84 and 86. In the case of elastic elements that do not conform to Hooke's law, such as constant-force springs, the counterbalancing force will remain the same. The amount of cord 112 extending out of guide tube 134 is shown as length L1.

Figure 4C:
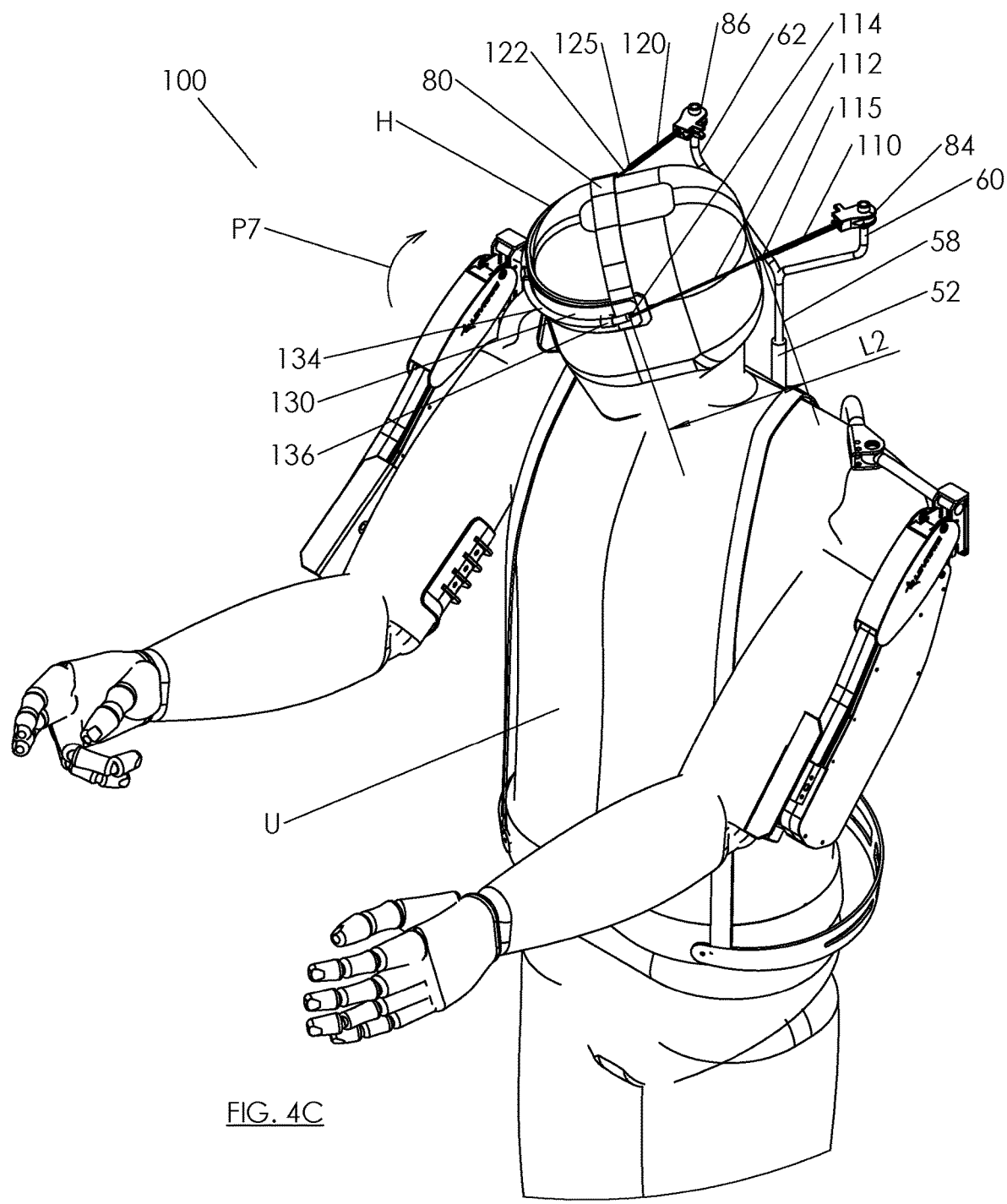

FIG. 4C shows the arm support system 100 with the user's head declined and rotated to the right, approximately along path P7. In response to the rotation of the user's head to the right, the amount of cord 112 extending out of guide tube 134 has increased, as cord 112 slides within guide tube 134, and is shown as length L2. The length of the elastic elements 110 and 120 has remained basically the same, and thus provide the same counterbalancing force as before, and are not further extended by the rotational motion of the user's head. Any extension of the elastic elements 110 and 120 is isolated from the side-to-side motion of the user's head H, and is instead only responsive to the declination of the user's head H, as desired.

Figure 5:
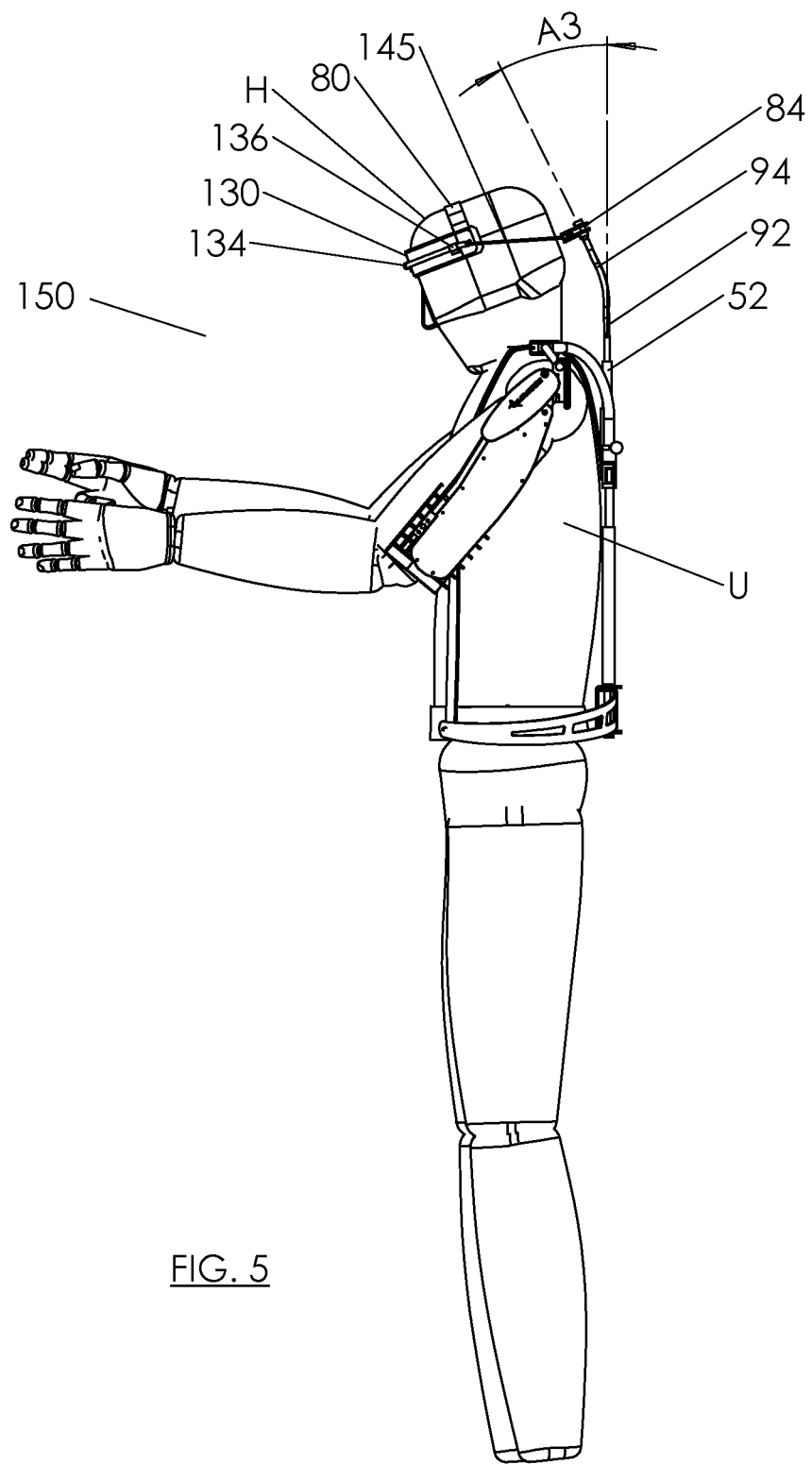
FIG. 5 is a side view of still another embodiment of a head support system supporting the head of the user.

FIG. 5 shows another exemplary embodiment of an arm support system 150 similar to the one shown in of FIGS. 4A-4C, with the user's head declined, with the flexibility of the head support being provided by the Y-frame bars and post. Y-frame post 92 and Y-frame bar 94 are shown deflected (approximately along arc A3) as the user works with their head H declined. Cord 145, attached to Y-frame bar 94 by buckle 84, may be substantially inelastic. Cord 145 may slide within guide tube 134 in response to side-to-side motion of the user's head, as described in reference to FIG. 4A-C. Thus, in this embodiment, the Y-frame bar 92 and/or Y-frame 94 may be elastically deflectable to accommodate declining the head H while providing a supporting force, while the inelastic core 145 may simply slide within the guide tube 134 to accommodate turning of the head H with minimal resistance.

Figure 6:
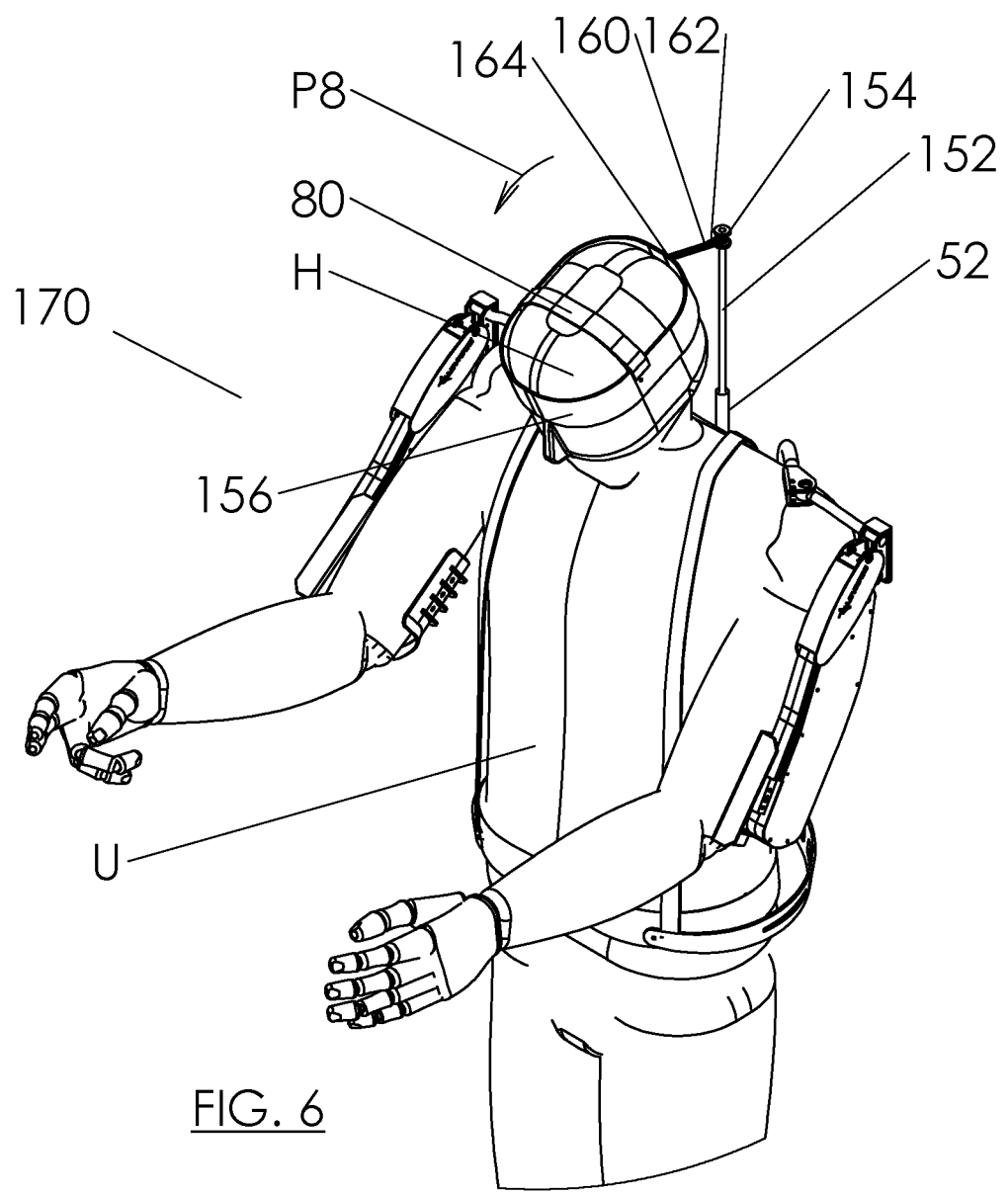
FIGS. 6 and 7 are perspective views of alternative embodiments of head support systems including a head band surrounding the head of the user.

FIG. 6 shows yet another exemplary embodiment of an arm support system 170 with the user's head declined. Unlike previous embodiments, the forehead band 76 or 130 is replaced with a headband 156, which may essentially encircle all of the user's head. Headband 156 may be flexible, semi-flexible, or rigid, as desired. Optional crown band 80 assists in keeping headband 156 properly positioned on the user's head. A single elastic element 160 provides the resilient support given by the dual elements described in previous embodiments.

For example, as shown, elastic element 160 is connected to the back of the headband 156 at location 164, and to support post 152 at connector 154. Support post 152 is joined to socket post 52, and thereby to the harness and/or frame of the arm support system 170 (as in previous embodiments). Elastic element 160 may be made from any known elastic material, such as latex rubber, silicone, or polyurethane elastomer, or may be formed from commonly known spring structures, such as coil springs or constant force springs. Elastic elements 160, in response to the user U working with their head H declined approximately along path P8, has extended and lengthened.

In the case of an elastic element that conforms approximately to Hooke's law, the force in the elastic element will increase as it extends, creating an increasing counterbalancing force to support the user's head H. The amount of counterbalancing force at a given position may be selected by the user, for example, by selecting an elastic element with more or less spring rate, or by adjusting the length of the elastic element with connector 154. In the case of an elastic element that does not conform to Hooke's law, such as a constant-force spring, the counterbalancing force will remain the same. Optionally, the connector 154 may incorporate the elastic element adjustment function similar to the buckles 84 and 86 referred to in the description of FIG. 2-4.

Figure 7:
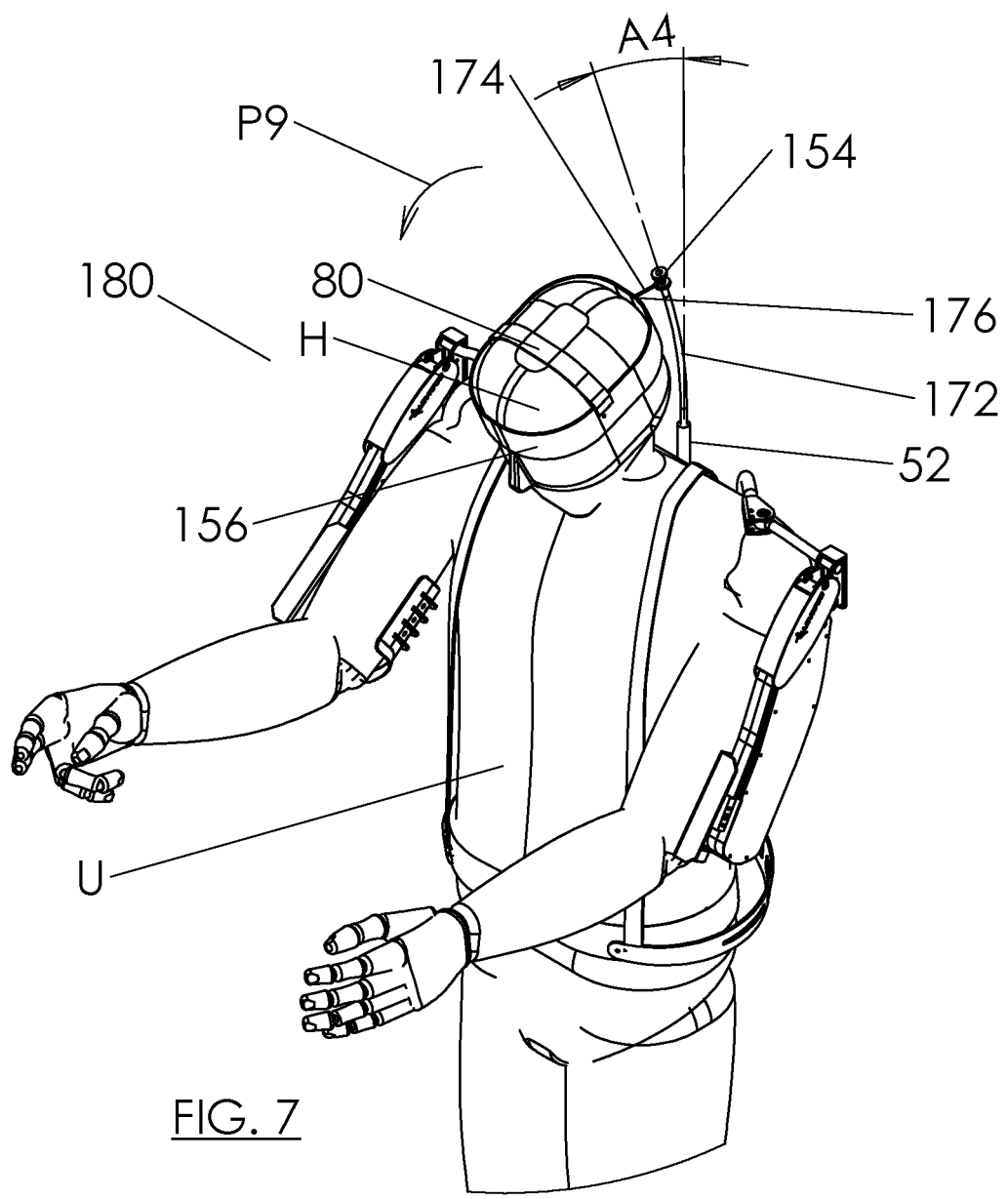

FIG. 7 shows still another exemplary embodiment of an arm support system 180 that is a variant of arm support system 170 shown in FIG. 6, with the flexibility of the head support being provided by support post 172. Headband 156 may be flexible, semi-flexible, or rigid. Optional crown band 80 assists in keeping headband 156 properly positioned on the user's head. A single inelastic cord 174 is connected to the back of headband 156 at point 176, and to support post 172 at connector 154. Support post 172 is joined to socket post 52, and thereby to the harness and/or frame of the arm support system 180 (as in previous embodiments). User U is shown with their head H declined approximately along path P9. Support post 172, in response, has deflected approximately along arc A4, and is providing a counterbalancing force on the user's head, e.g., acting as a leaf spring. Cord 174 (inelastic) remains approximately the same length.

Figure 8A:
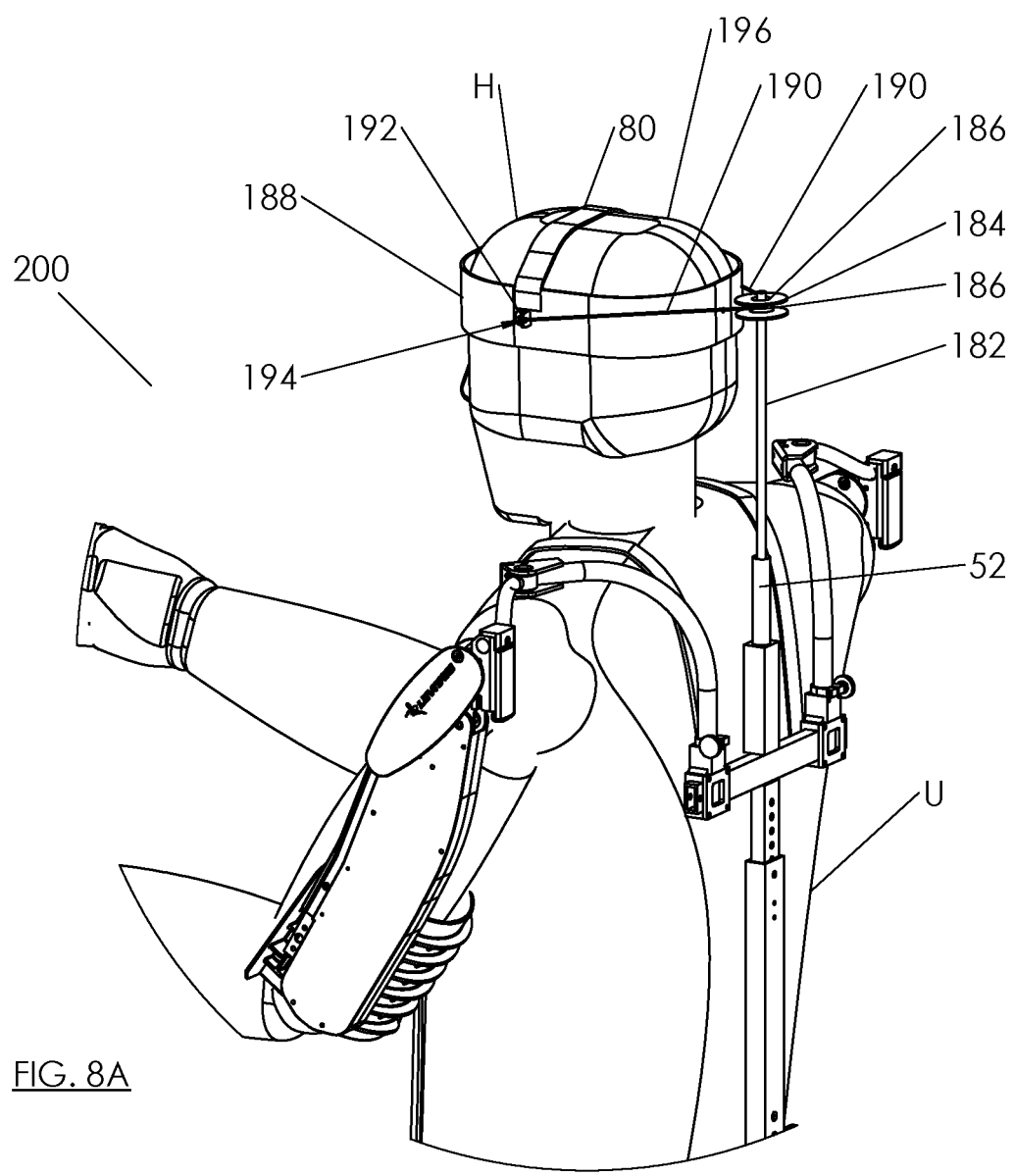
FIGS. 8A-9B show alternative embodiments of a head support system including one or more pulleys that enhance mobility of the user's head.
Figure 8B:
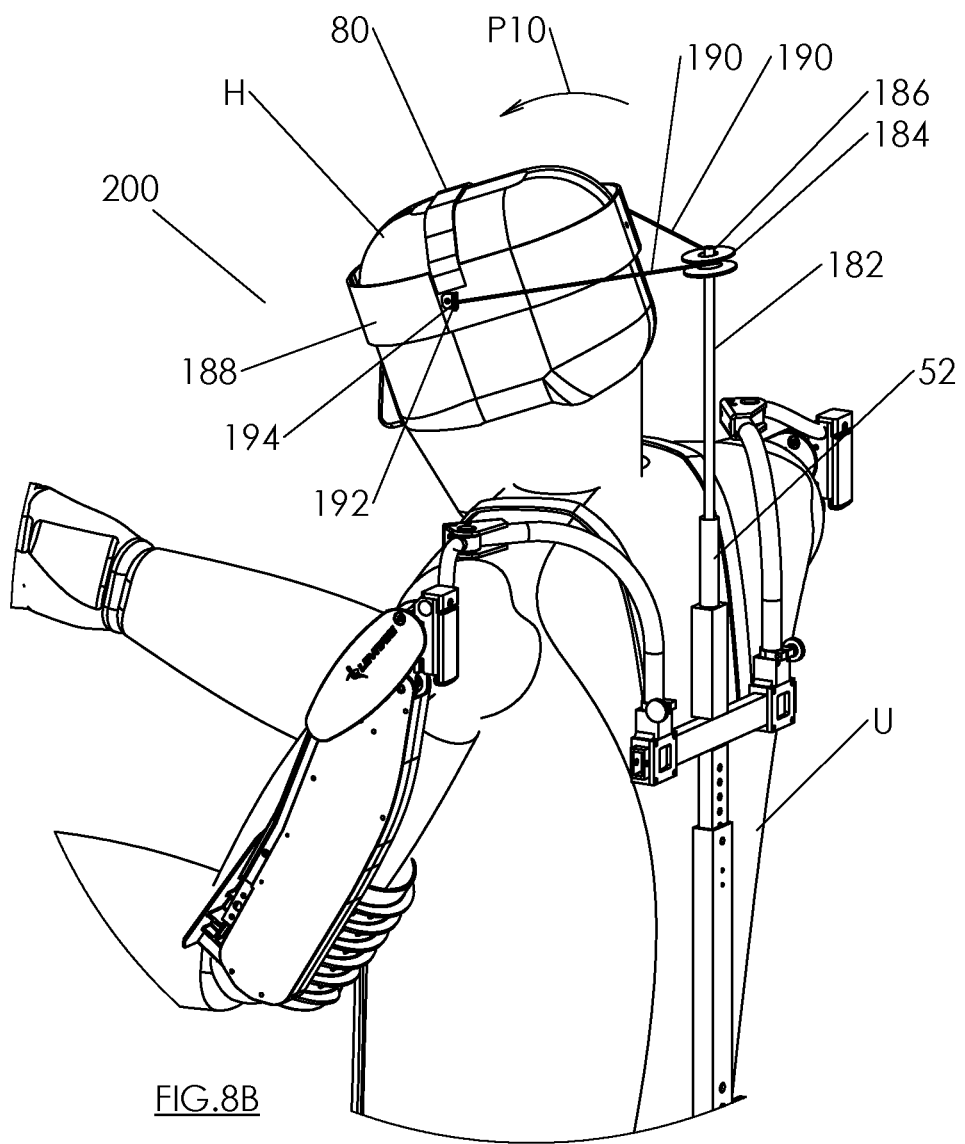

Turning to FIGS. 8A and 8B, another exemplary embodiment of an arm support system 200 is shown that is a variant of arm support system 170, with a pulley providing additional mobility. Headband 188 may essentially encircle all of the user's head, and may be flexible, semi-flexible, or rigid. Optional crown band 80 assists in keeping headband 188 properly positioned on the user's head. A single elastic element 190, joined to the sides of headband 188 at locations 194 and 196 (location 196, not shown, is approximately opposite location 194), provides resilient support. Elastic element 190 lies within groove 186 of pulley 184. Pulley 184 may freely rotate about support post 182 on hub 188, e.g., using a rolling element (ball or roller) bearing, a bushing, or may a spherical bearing that permits pulley 184 to tilt in response to the angle of elastic element 190.

FIG. 8B shows the arm support system of FIG. 8A with the user's head declined, approximately along path P10. Elastic element 190 has extended and lengthened in response. Pulley 184, able to freely rotate about support post 182 on hub 188, eases motion of elastic element 190 about support post as user U rotates their head from side to side.

As in other embodiments, alternatively, instead of (or in addition to) an elastic element 190, the elastic element 190 may be replaced with an inelastic cord (not shown), and the supporting force of the head support may be provided by a deflectable support post (182 in this version), e.g., biased to a straight or other configuration, yet elastically deflectable to accommodate declining the head H.

Figure 9A:
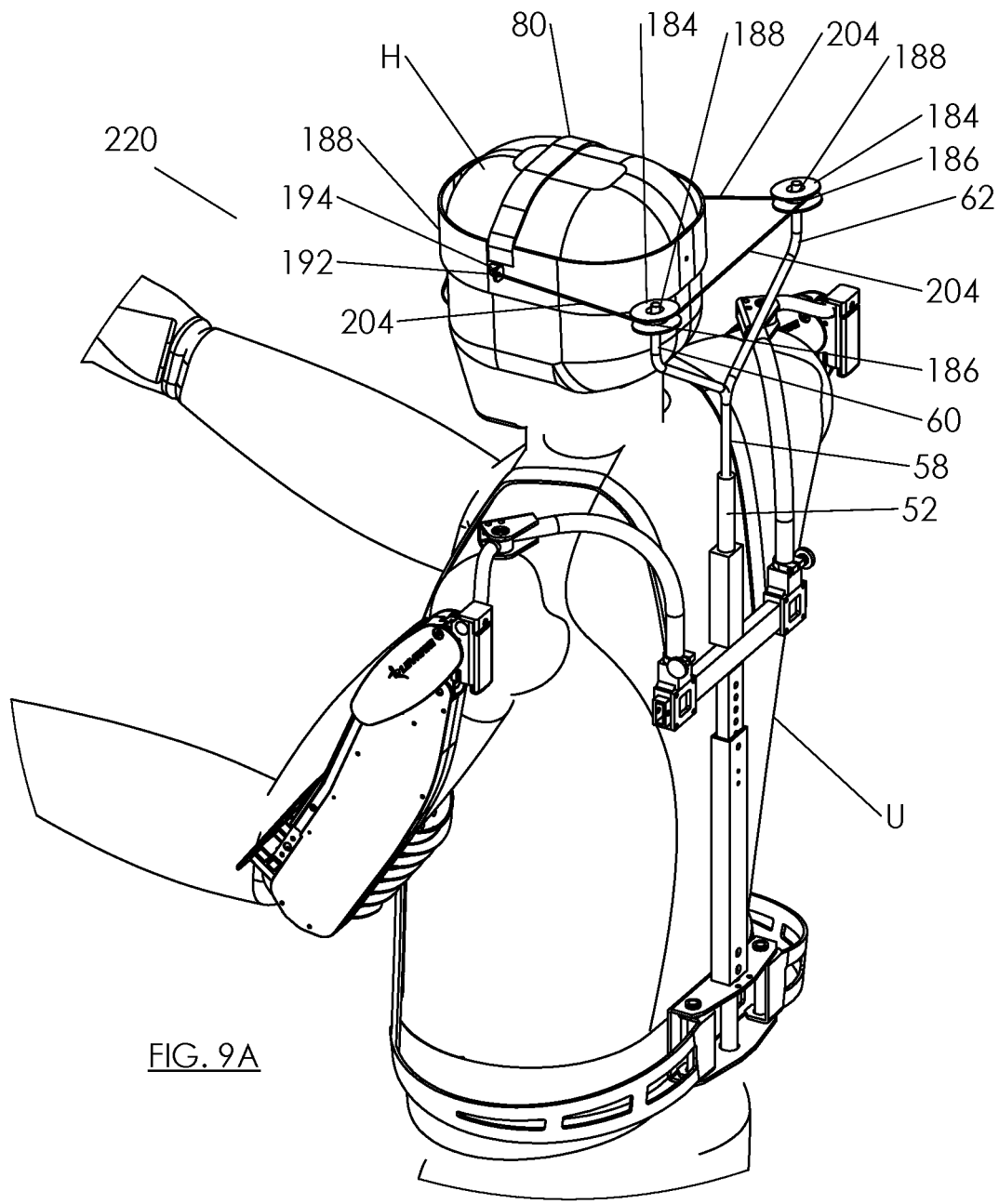
Figure 9B:
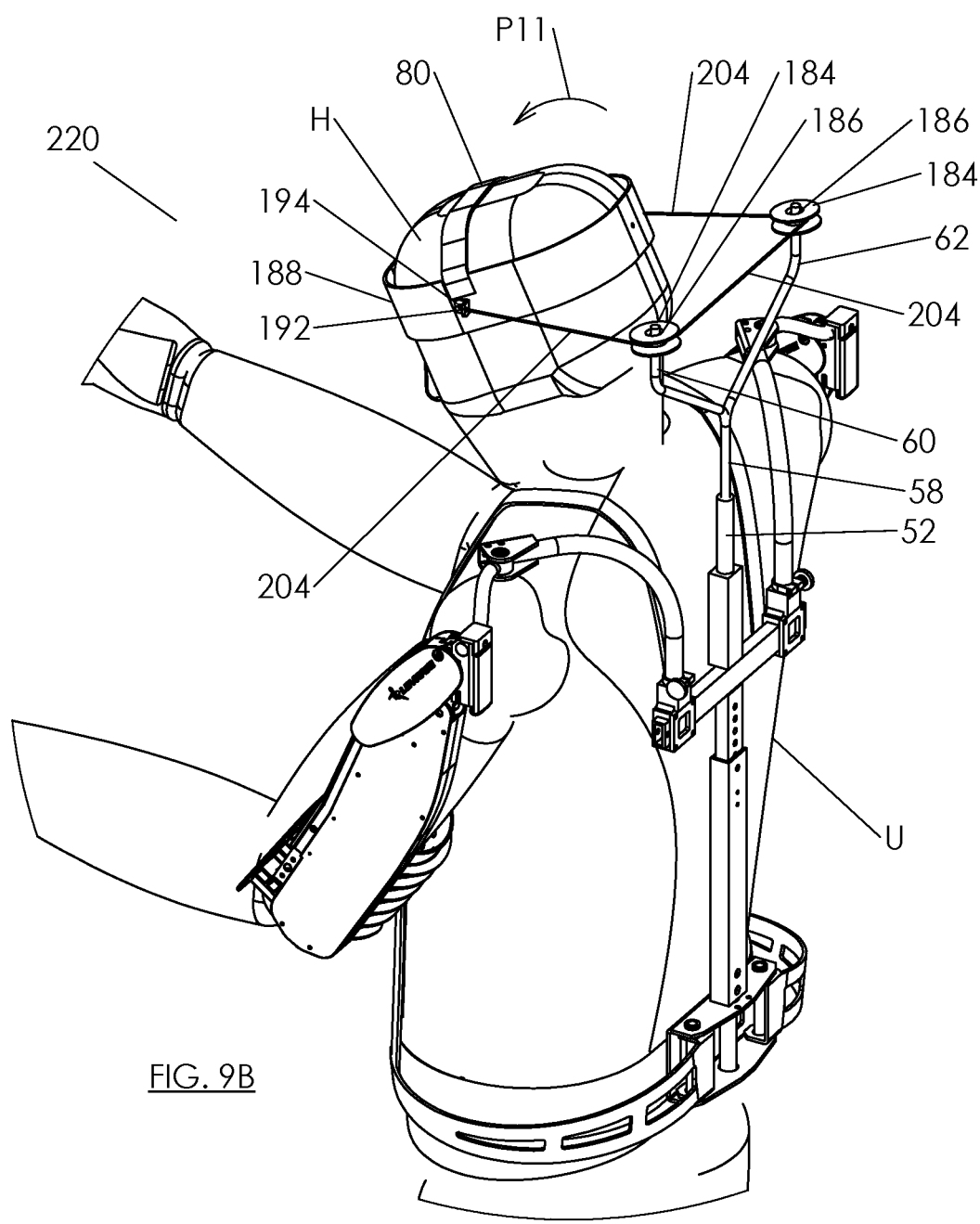

Turning to FIGS. 9A and 9B, another embodiment of an arm support system 220 is shown that is a variant of arm support system 200 shown in FIGS. 8A and 8B, with a pair of pulleys providing additional mobility rather than a single pulley. As shown, headband 188 may essentially encircle all of the user's head, and may be flexible, semi-flexible, or rigid. Optional crown band 80 assists in keeping headband 188 properly positioned on the user's head. Alternatively, a forehead band may be provided instead of the headband 188, if desired.

A single elastic element 204, joined to the sides of headband 188 (or ends of a forehead band, not shown) at locations 194 and 196 (location 196, not shown, is approximately opposite location 194), provides resilient support. Elastic element 204 lies within grooves 186 of pulleys 184. Pulleys 184 may freely rotate about Y-frame bars 60 and 62 on hubs 188, which may be rolling elements, e.g., (ball or roller) bearings, bushings, or may be spherical bearings, which permit pulleys 184 to tilt in response to the angle of elastic element 204.

FIG. 9B shows the arm support system 220 with the user's head declined, approximately along path P11. Elastic element 204 has extended and lengthened in response. Pulleys 184, able to freely rotate about Y-frame bars 60 and 62 on hubs 188, ease motion of elastic element 204 about Y-frame bars 60 and 62 as the user U rotates the head H from side to side.

As in other embodiments, an additional variant (not shown) has the flexibility of the head support being provided by the Y-frame bars and post (58, 60, and 62 in this version) rather than the elastic element 204.

Figure 10A:
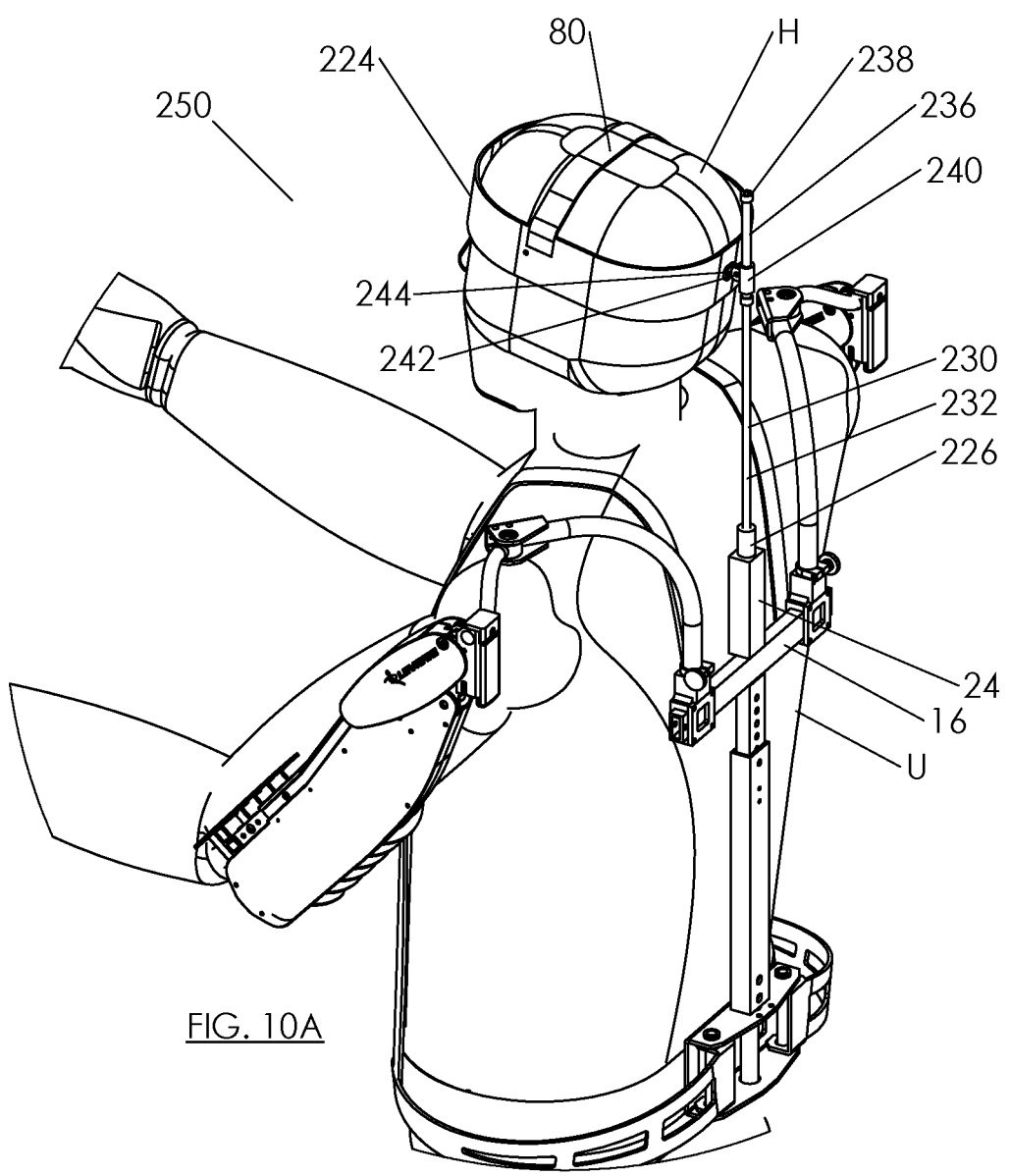
FIGS. 10A and 10B show another embodiment of a head support system including a resilient member support a headband supporting the user's head.
Figure 10B:
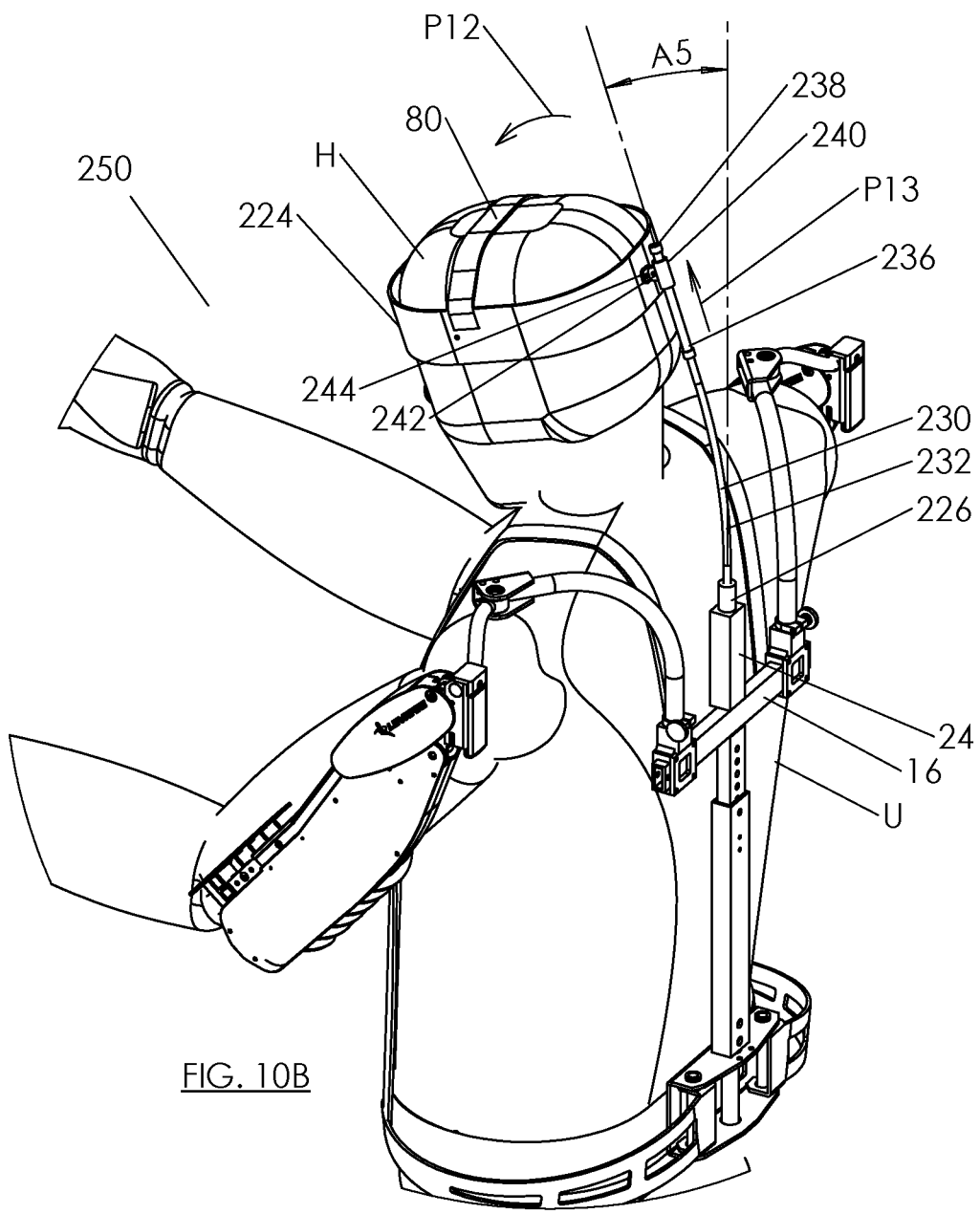

Turning to FIGS. 10A and 10B, yet another exemplary embodiment of an arm support system 250 is shown that includes a head support feature that employs a resilient element structure 230, e.g., including a resilient rod 232, similar to that disclosed in U.S. Publication No. 2014/0033391. Headband 224 may essentially encircle all of the user's head, and may be flexible, semi-flexible, or rigid. Optional crown band 80 assists in keeping headband 224 properly positioned on the user's head.

Pivot mount 242 is attached to headband 224, and includes pivot point 244. Slide mount 240 attaches to pivot mount 242 at pivot point 244, using known fastening elements such as screws or pins. Slide mount 240 encircles slide rod 236, and may freely translate and rotate relative to it. Resilient rod 232, joined to one end of slide rod 236, provides a counterbalancing force to support the user's head H. For example, the rod 232 may be biased to a substantially straight or other orientation, yet may be resiliently bendable to accommodate declining the head H, thereby providing a restoring force given the bias to the substantially straight orientation. Resilient rod 232 may be made from metal, plastic, or other appropriate resilient material. The other end of resilient rod 232 is mounted (optionally pivot-ably) in socket post 226, which is located in frame socket 24. In FIG. 10A, the user's head H is shown non-declined, and the resilient rod 232 is relatively straight, and therefore is applying relatively little restoring force to the user's head H. Optionally, more than one resilient element structure 230 may be used to achieve the desired counterbalancing force.

FIG. 10B shows the arm support system 250 with the user's head H declined, approximately along path P12. In response, the resilient rod 232 is shown deflected approximately along arc A5. In this deflected position, the resilient rod 232 provides a counterbalancing force to support the user's head H. The slide mount 240 may translate along slide rod 236 approximately along path P13, in order to accommodate the change in position and angle of the user's head.

Figure 11A:
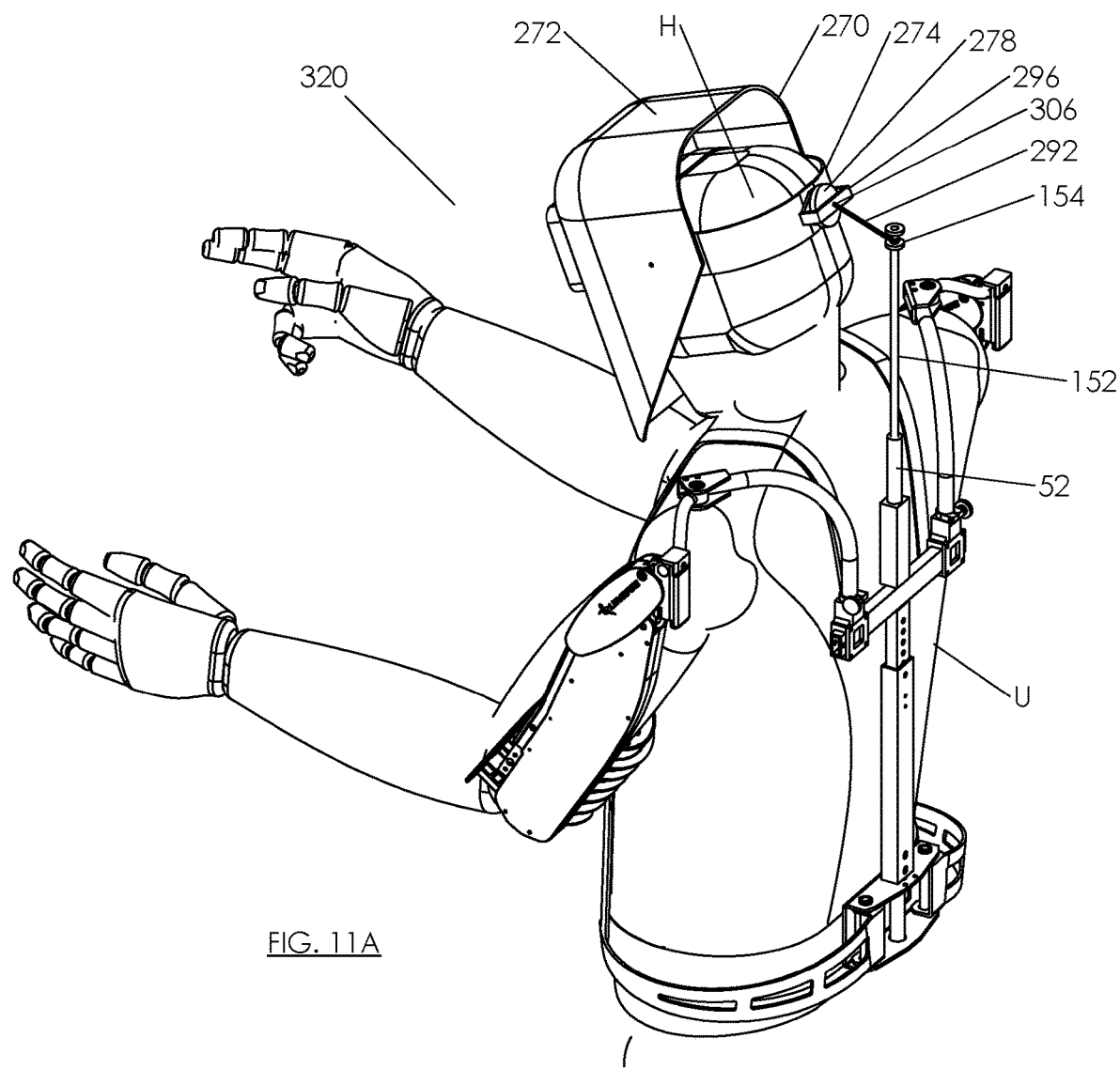
FIGS. 11A-11C show yet another embodiment of a head support system similar to the support system shown in FIG. 6 providing a counterbalancing force to headgear worn by the user.

FIG. 11A shows still another exemplary embodiment of an arm support system 320 that is a variant of arm support system 170 of FIG. 6, intended for use when the user U is wearing existing headgear in the performance of their work. Examples of such headgear include protective helmets, head-mounted lamps, and head-mounted magnification glasses. In these cases, the user U is already wearing a headband, as part of the existing equipment, which might interfere with the forehead band 76 or headband 156 described previously. For example, as shown in FIG. 11A, user U is wearing a common welding helmet 270, which includes a shield 272, headband 274, and adjustment knob 278. A clip 296 is shown attached to the welding helmet 270 at adjustment knob 278. Elastic element 292 is attached to clip 296 at point 306, and to support post 152 at connector 154. Support post 152 is located in socket post 52 and thereby to the harness and/or frame of the arm support system 320 (which may be similar to any of the previous embodiments). Elastic element 292, joined in this way to the clip 296 attached to the welding helmet 270, provides a counterbalancing force to support the user's head H.

Figure 11B:
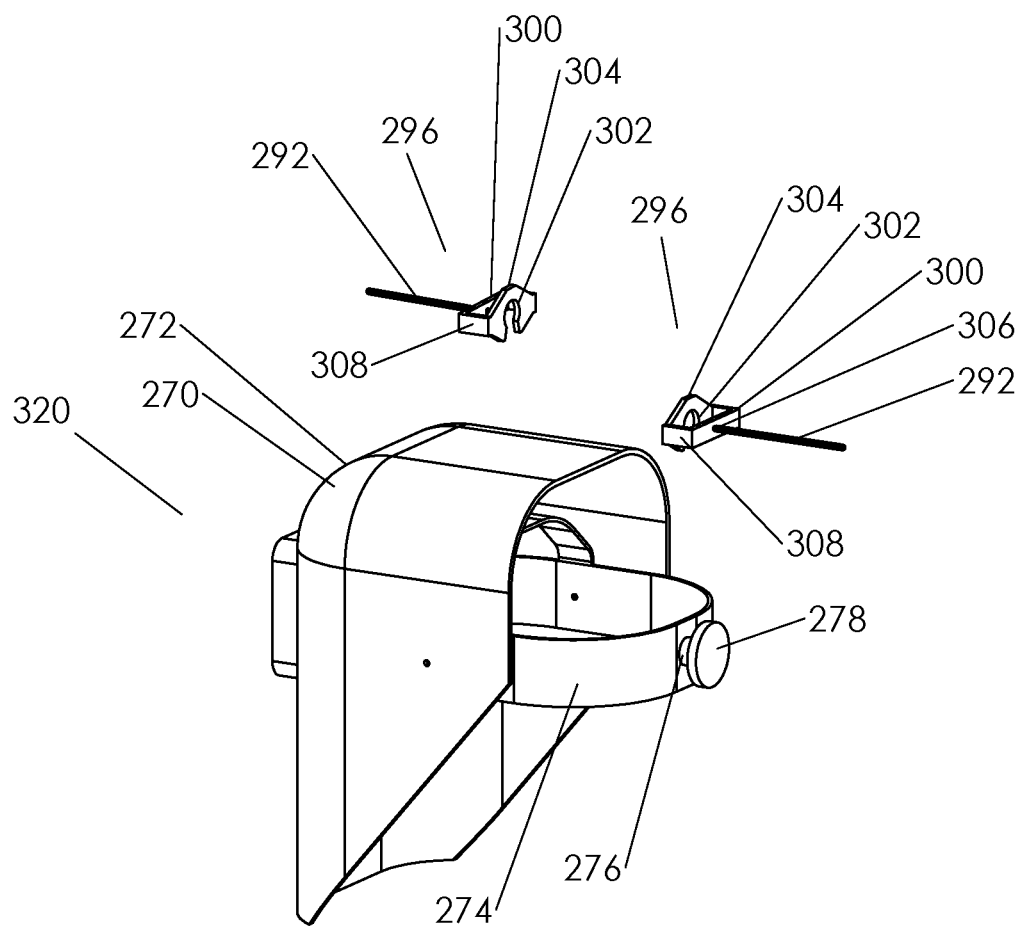

FIG. 11B shows a detail of the welding helmet 270 of FIG. 11A, showing features of the helmet and clip 296 (clip 296 shown from two sides). Helmet adjustment knob 278 may be attached to headband 274 by neck 276, which has a smaller diameter than adjustment knob 278. Clip 296 has a front plate 304 that includes a notch 302. Notch 302 is sized to fit over neck 276, but to interfere with adjustment knob 278. Side straps 308 join front plate 304 to back plate 300, and may provide a space between front plate 304 and back plate 300 that accommodates adjustment knob 278. Side straps 308, front plate 304, and back plate 300 may be flexible, rigid, or semi-rigid. Elastic element 292 attaches to back plate 300 at attachment point 306.

Figure 11C:
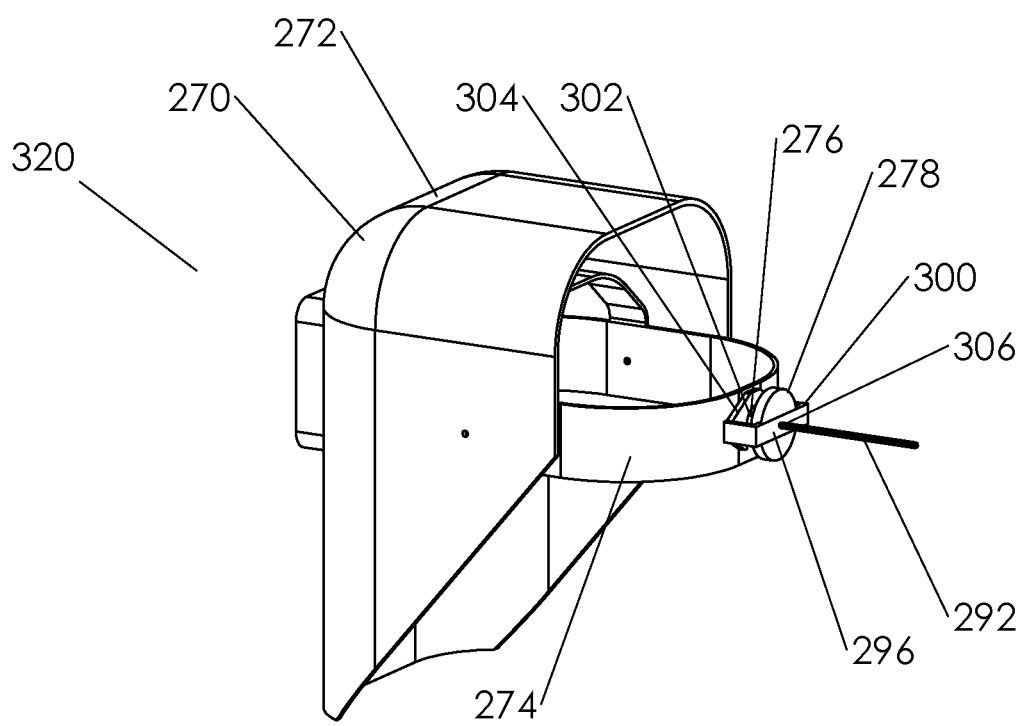

FIG. 11C shows a detail of FIG. 11B with the clip 296 shown fully attached to the welding helmet 270. Clip 296 holds on to adjustment knob 278, allowing elastic element 292 to provide a counterbalancing force to support the user's head H.

Figure 11D:
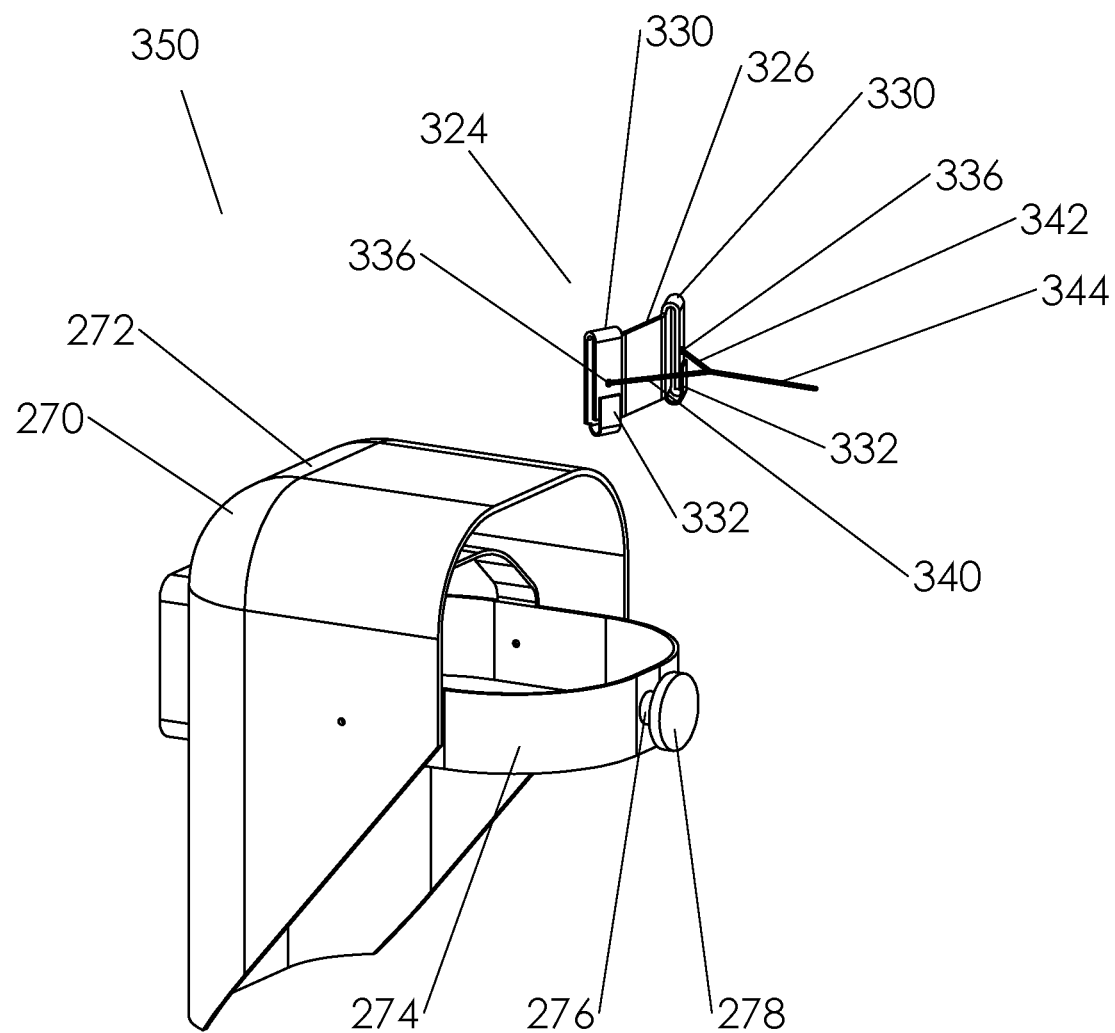
FIGS. 11D and 11E are details showing an alternative embodiment of a clip for attaching the headgear to a head support system, such as the system shown in FIGS. 11A-11C.

FIG. 11D shows an alternative clip 324 for existing headgear, such as welding helmet 270. Backplane 326 is joined to straps 330, which in turn provide attachment points 336 for elastic elements 340 and 342. Elastic elements 340 and 342 may be joined to a single elastic element 344. Backplane 326 and straps 330 may be flexible, rigid, or semi-rigid.

Figure 11E:
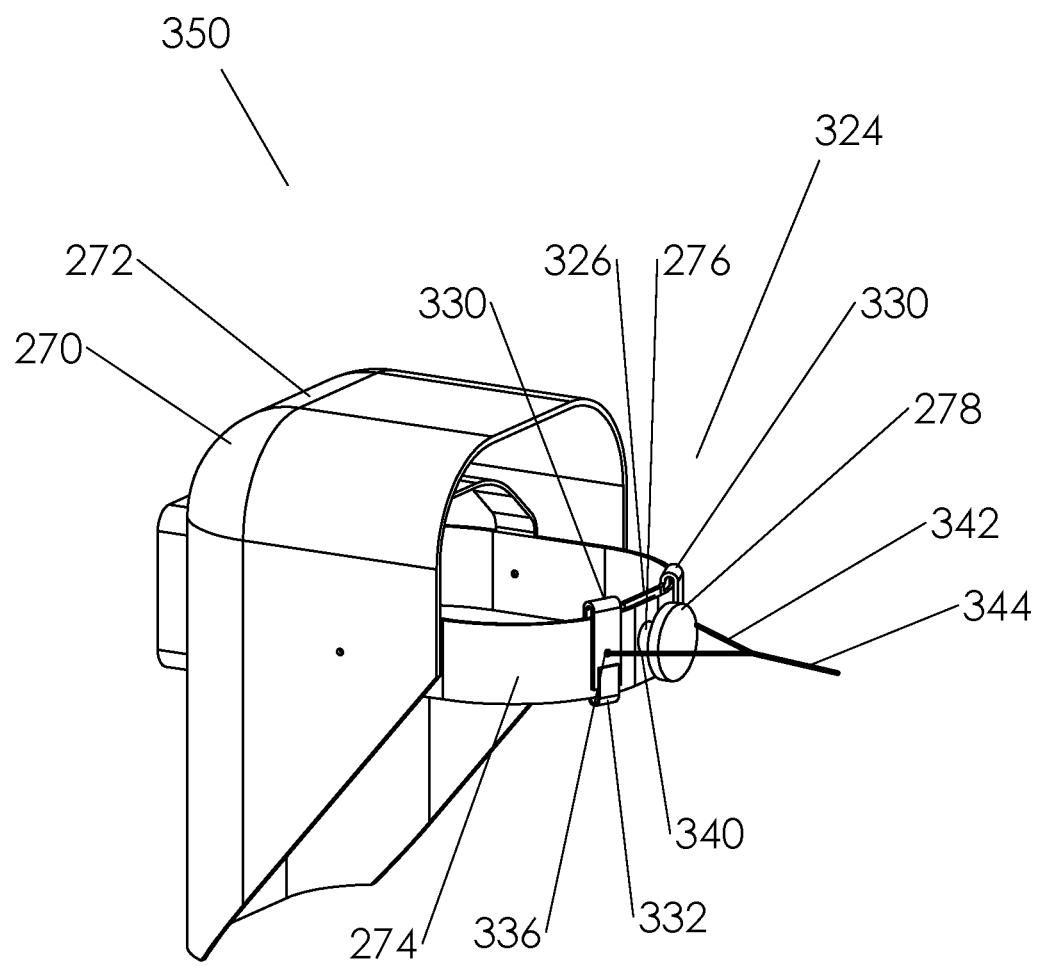

FIG. 11E shows the alternative clip 324 of FIG. 11D fully attached to welding helmet 270. Backplane 326 is located on the inside of headband 274. Straps 330 reach over the top of headband 274, and terminate on the outside of headband 274. Optional securing straps 332 may reach under the headband 274 and attach to straps 330 using known connectors, such as Velcro or snaps, for additional security. Clip 324 thus holds on to headband 274, allowing elastic elements 340, 342, and 344 to provide a counterbalancing force to support the user's head H.

Figure 12A:
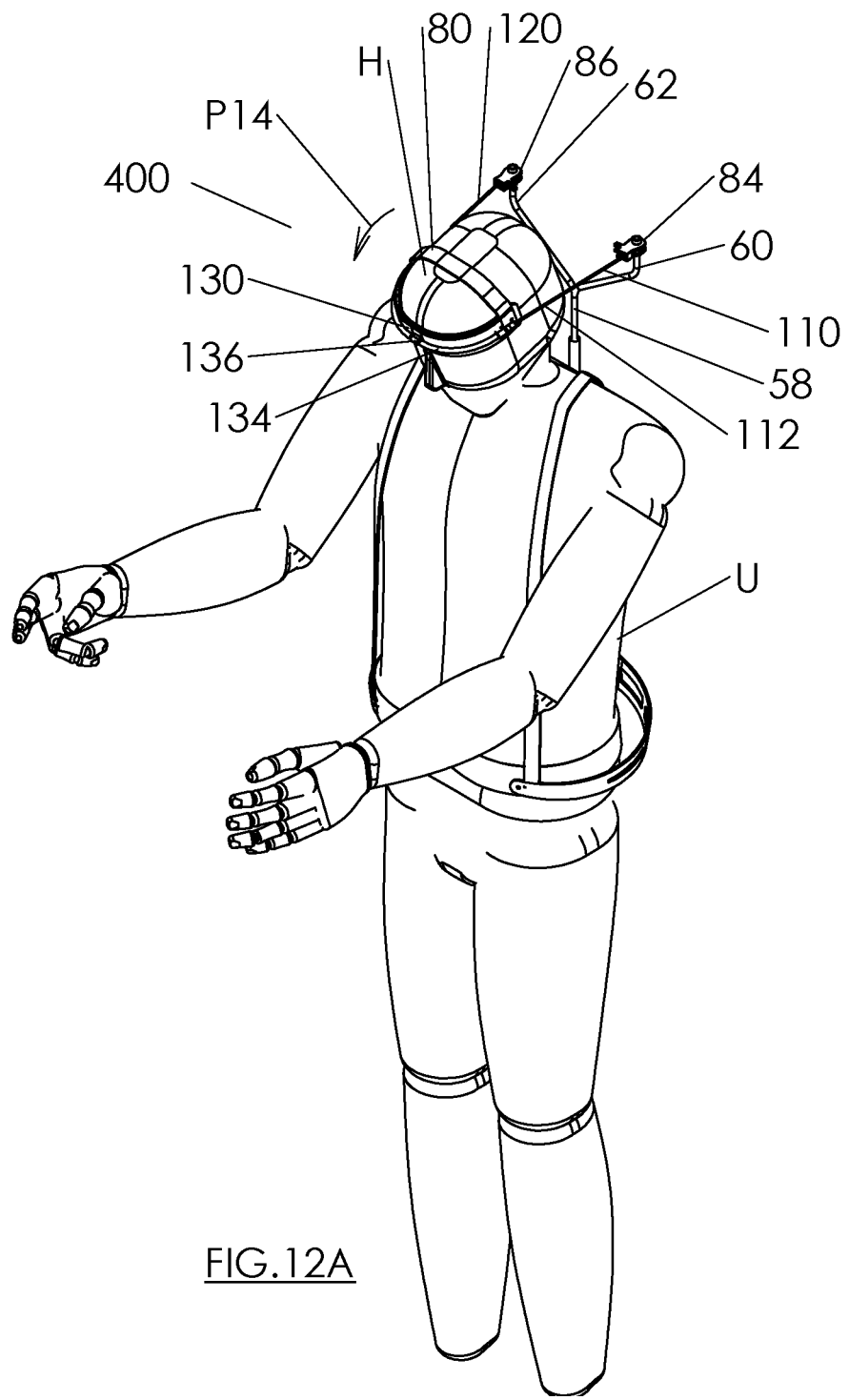
FIGS. 12A and 12B are perspective views of another embodiment of a head support system.
Figure 12B:
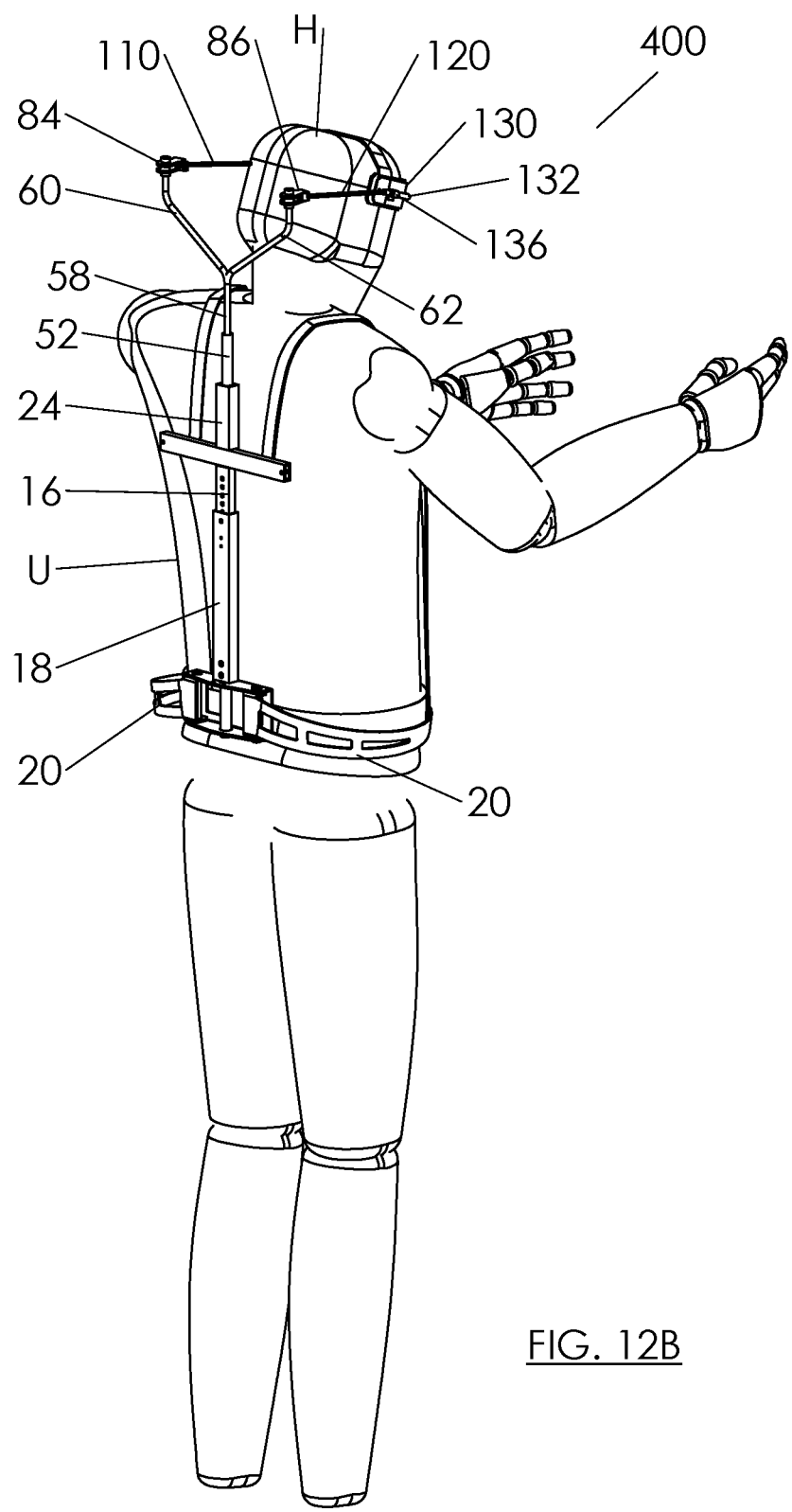

Turning to FIGS. 12A and 12B, another exemplary embodiment of a head support system 400 is shown, similar to the system 100 of FIGS. 4A-4C without the arm support function. User U is shown wearing the frame and head support elements of FIGS. 4A-4C, with their head H declined approximately along path P14. Forehead band 130, which may be flexible, semi-flexible, or rigid, is located on the user's forehead F. Crown band 80 assists in properly locating the forehead band 130. A guide tube 134 is secured to forehead band, for example by guide tube clips 136. Guide tube 134 may be rigid or flexible, and may be made from, or lined with, a low friction material such as PTFE or Nylon. Guide tube 134 provides a track in which cord 112 may slide. A lubricant (not shown) may aid in smooth sliding motion of the cord 112 within guide tube 134. Smooth sliding motion of the cord 112 within the guide tube 134 facilitates rotation of the head H from side to side. Cord 112 is joined to elastic element 110 at coupling 115. Elastic element 110 is in turn joined to Y-frame bar 60 at buckle 84. The equivalent elastic element 120, joined to the other end of cord 112 at coupling 125, is joined to Y-frame bar 62 at buckle 86.

FIG. 12B shows the head support system 400 from the back. Y-frame post 58, which supports and locates Y-frame bars 60 and 62, is joined to socket post 52. Socket post 52 is inserted into frame socket 24, and may be able to rotate relative to frame socket 24 as previously described. Socket post 52 may also be adjustable vertically relative to frame socket 24, by the use of commonly known components, as previously described. Y-frame post 58 and Y-frame bars 60 and 62 may be rigid or flexible, or may be formable by bending in order to shape them as desired. Frame socket 24 is joined to frame T 16, which in turn connects to spine tube 18, which is joined to belt strut(s) 20. Frame socket 24, frame T 16, spine tube 18, and belt strut(s) 20 provide a substantially rigid structure by which loads such as the weight of the user's head is transferred through flexible elements onto the user's torso and hips.

Figure 13A:
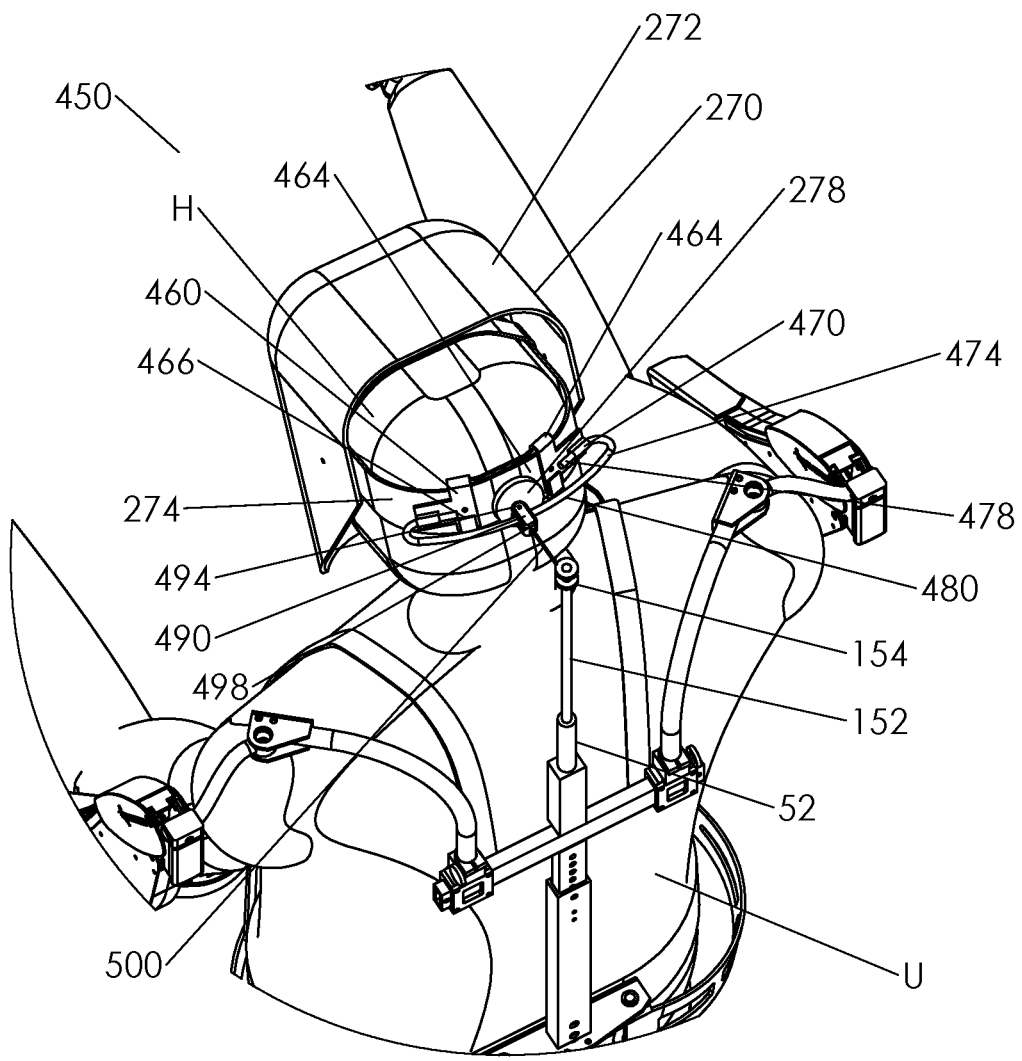
FIGS. 13A-13C show another embodiment of a head support system providing a counterbalancing force to headgear worn by the user.
Figure 13B:
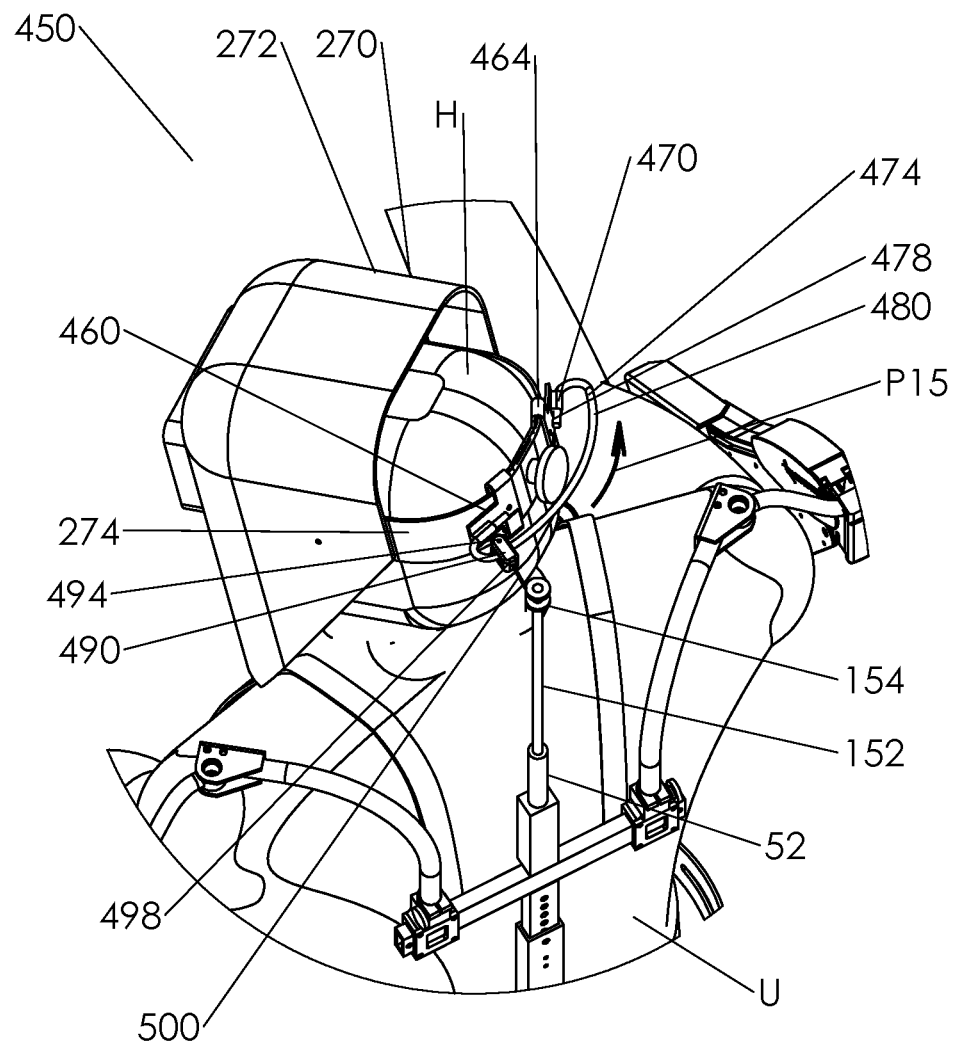
Figure 13C:
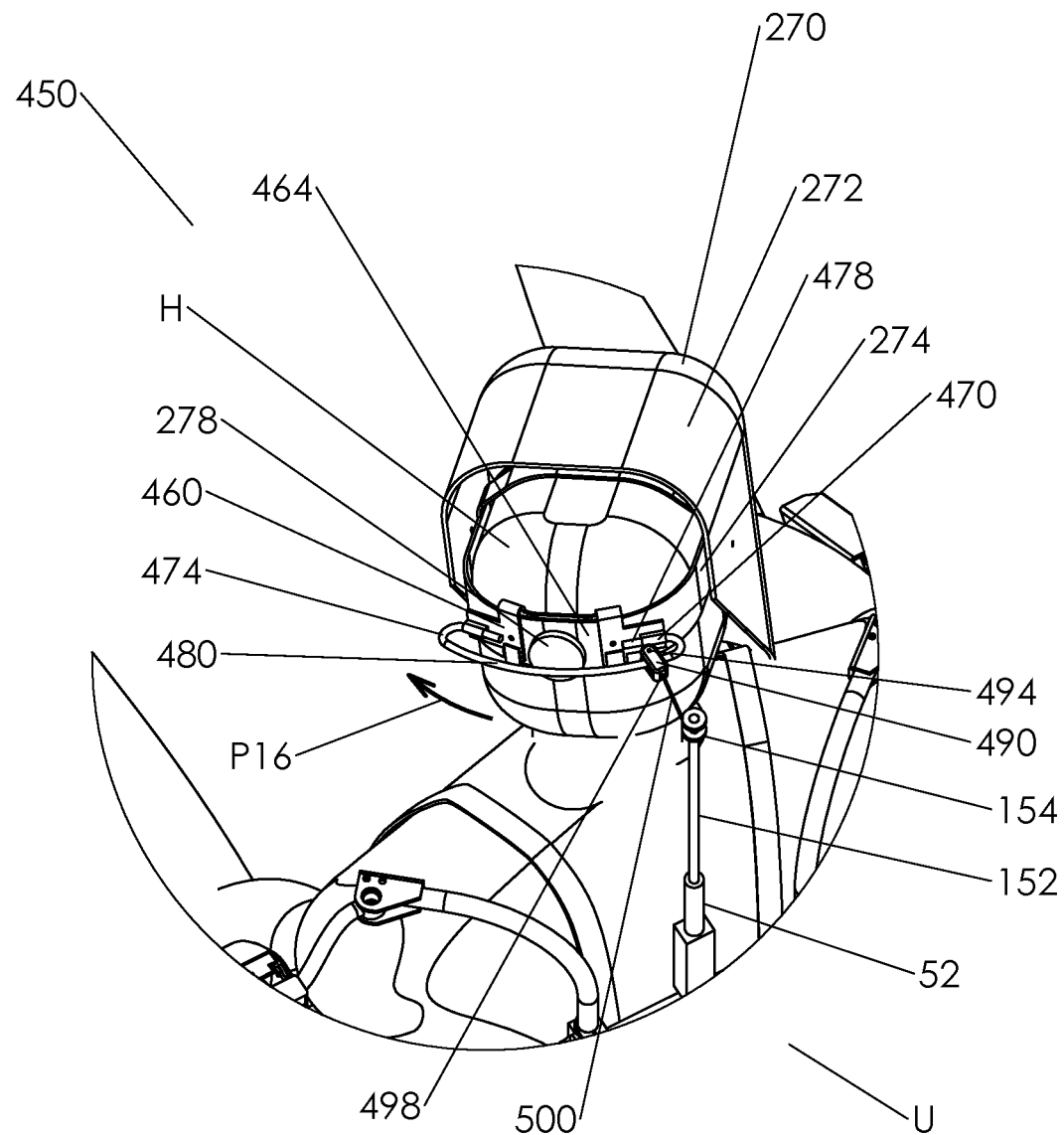

Turning to FIGS. 13A-13C, another exemplary embodiment of an arm support system 450 is shown that is a variant of arm support system 320 of FIG.11D, e.g., intended for use when the user U is wearing existing headgear in the performance of their work. Examples of such headgear include protective helmets, head-mounted lamps, and head-mounted magnification glasses. In these cases, the user U is already wearing a headband, as part of the existing equipment, which might interfere with the forehead band 76 or headband 156 described previously. Shown in FIG. 13A is a user U wearing a common welding helmet 270, which includes a shield 272, headband 274, and adjustment knob 278. Alternative clip 460 is shown fully attached to welding helmet 270, in the same way as alternative clip 324 of FIG. 11D. Backplane 462 (equivalent to 326 of FIG. 11D, not shown) is located on the inside of headband 274.

Straps 464 reach over the top of headband 274, and terminate on the outside of headband 274. Optional securing straps 466 may reach under the headband 274 and attach to straps 464 using known connectors, such as Velcro or snaps, for additional security. Clip 460 provides a mounting surface for back rail 474, which includes rail ends 478 and rail body 480. Rail ends 478 are attached to clip 460 at rail pivots 470, and may optionally be free to rotate within rail pivots 470, if desired. Rail body 480 provides a track for clevis 490, which is free to travel along rail body 480 in response to motion of the user's head H. Thus, the user may be free to rotate the head H from side to side with the clevis 490 sliding along the rail body 480 to maintain the clevis 490 substantially centered behind the user's head H adjacent the support post 152.

Rail body 480 may be curved, straight, have varying curvatures, or may curve in three dimensions, as desired by the user. Rail body 480 may be rigid, semi-rigid, and/or may be formed into different shapes as desired by the user. The length of rail body 480 may be varied as needed to increase the range of motion of the user's head. Finally, rail body 480 may have different cross-sections, such as round, rectangular, oval, or other desirable shapes.

Clevis 490 encloses rail body 480, for example, by a pin 494 that holds the clevis 490 onto rail body 480. An optional rotational element may be provided within the clevis 490 (not shown) that rotates about pin 494 to reduce friction as the clevis 490 moves along the rail body 480, such as a roller or a wheel. Clevis 490 also includes attachment location 498, to which tension element 500 attaches. The other end of tension element 500 attaches to support post 152 at connector 154. Support post 152 is secured in socket post 52 and thereby to the frame of the arm support system 450 (which may be similar to any of the previous embodiments). Thus, the tension element 500, joined in this way to the clip 460 via the back rail 474 and clevis 490, is thereby coupled between the welding helmet 270 and to the support post 152, and is thus able to provide a counterbalancing force to support the user's head H.

Tension element 500 may be elastic, inelastic, or a combination of both. Tension element 500, if elastic, provides a counterbalancing force to the weight of the user's head H that varies as the user declines or raises their head. For example, if the user has their head generally upright, and does not need much counter-balancing force, the elastic tension element 500 may be relatively un-tensioned, and is therefore not providing much counterbalancing force. If the user declines their head, and more counter-balancing force is desirable, elastic tension element 500 extends, and following Hooke's law, applies a greater counter-balancing force. Tension element 500 may optionally be elastic but not conform to Hooke's law, e.g., a constant force spring. If tension element 500 is inelastic, support post 152 or other components of the frame of the arm support system may be deflectable, e.g., flexible or elastic, to provide a counterbalancing force for the weight of the user's head that varies as the head is declined (as described in reference to previous embodiments).

FIG. 13B shows the arm support system 450 with the user's head H declined, and rotated generally toward their left shoulder. In response to this motion, the back of the user's head H moves approximately along path P15, as does the back rail 474. Clevis 490, free to slide (or roll) along the rail body 480, remains in approximately the same place relative to the support post 152 as it was in FIG. 13A. Because the clevis 490 remains in approximately the same position as it was originally, the tension element 500 is not required to extend in response to the rotational (side-to-side) motion of the user's head H, and is thus not further extended by that side-to-side motion. In this way, any extension of the tension element 500 is isolated from the side-to-side motion of the user's head H, and is instead only responsive to the declination of the user's head H, as desired.

FIG. 13C shows the arm support system 450 with the user's head H declined, and rotated generally toward their right shoulder. In response to this motion, the back of the user's head H moves approximately along path P16, as does the back rail 474. Again, the clevis 490, free to slide (or roll) along the rail body 480, remains in approximately the same place relative to the support post 152 as it was in FIG. 13A. As described in relation to FIG. 13B, any extension of the tension element 500 is isolated from the side-to-side motion of the user's head H, and is instead only responsive to the declination of the user's head H, as desired.

Any of the other variants of head supports shown previously may also be used without the arm support function, i.e., as a stand-alone head support system. Optionally, in any of the embodiments herein, at least a portion of the head support may be removable, e.g., a base of the Y-frame bar may be removably mountable to the harness, e.g., to allow the head support to be removed when not needed, e.g., similar to the embodiment shown in FIG. 2B.

Additionally, any of the head support components shown previously, such as the forehead band 130, crown band 80, guide tube 134, guide tube clips 136, cord 112, elastic elements 110 and 120, Y-frame bars and post 60, 62, and 58, and buckles 84 and 86, may be either re-usable or disposable.

It will be appreciated that the devices, systems, and methods described herein may be used to support a user's head during a variety of tasks, e.g., during surgery, manufacturing, construction, and/or other activities. The systems generally allow the user to move their head freely while performing tasks, e.g., to rotate and/or bend their head forward, while providing an offsetting force to the user's head, e.g., to prevent or reduce fatigue. The offsetting force applied to the user's head as the user leans forward or bends their head forward may be variable, e.g., by modifying the profile of the spring or potential force generated by the cord, the frame, and/or other components of the system, as described elsewhere herein.

It will be appreciated that elements or components shown with any embodiment herein are merely exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

I claim:

1. A system for supporting a head of a user, comprising:
   a harness configured to be worn on a body of a user, the harness including a shoulder harness configured to be worn over or around one or both shoulders of the user; and
   a head support comprising:
      a support bracket comprising a first end mounted to the harness at a location such that a second end of the support bracket is configured to be positioned adjacent the head of a user wearing the harness;
      a rest member coupled to the second end of the support bracket such that the rest member is configured to extend at least partially around the head of the user to contact the user's forehead when the harness is worn;
      a rail on the rest member; and
      a clevis coupled to the second end of the support bracket to couple the rest member to the support bracket and slidable on the rail such that rotation of the head between left and right positions causes the clevis to slide along the rail, the head support configured to accommodate the user deflecting the head forward from a rest position while providing a counterbalancing force to at least partially support the weight of the head to prevent or reduce fatigue, wherein the second end of the support bracket is deflectable from a rest position and configured to accommodate the user deflecting the user's head forward when the rest member is worn yet is biased towards the rest position to provide the counterbalancing force.

2. The system of claim 1, further comprising an arm support coupled to the harness configured to support an arm of the user.

3. The system of claim 1, wherein the rail is removably coupled to the rest member by a clip.

4. A system for supporting a head of a user, comprising:
a harness configured to be worn on a body of a user, the harness including a shoulder harness configured to be worn over or around one or both shoulders of the user;
a head support comprising a support bracket comprising a first end mounted to the harness at a location such that a second end of the support bracket is positioned adjacent a back of the head of a user wearing the harness;
headgear configured to be worn on the user's head, the headgear comprising a band sized to extend around the back of the head of the user, the headgear coupled to the second end of the support bracket, the support bracket deflectable from a rest position to allow the user to decline the head and provide a counterbalancing force to at least partially support the weight of the head; and
a rail coupled to the band, and a clevis coupled to the second end of the support bracket to couple the headgear to the second end of the support bracket, the clevis slidable on the rail such that rotation of the head between left and right positions causes the clevis to slide along the rail without deforming the support bracket.

5. The system of claim 4, wherein the rail is removably coupled to the band by a clip.

6. The system of claim 4, further comprising a slide mount on the second end of the support bracket, the slide mount coupled to the clevis and configured to translate and rotate on the second end of the support bracket.

7. The system of claim 4, wherein the clevis is coupled to the second end of the support bracket by a cord including a first end coupled to the second end of the support bracket and a second end coupled to the clevis.

8. The system of claim 4, further comprising a cord including a first end connected to the clevis and a second end connectable to a connector for removably connecting the second end of the cord to the support bracket.

9. The system of claim 4, wherein the headgear comprises a welding helmet, a mask, a head-mounted lamp, or head-mounted magnification glasses.

10. The system of claim 4, wherein the headgear comprises a rest member that extends at least partially around the head of the user to contact the user's forehead when the harness is worn.

11. A system for supporting a head of a user, comprising:
a harness configured to be worn on a body of a user, the harness including a shoulder harness configured to be worn over or around one or both shoulders of the user;
a head support comprising a support bracket comprising a first end mounted to the harness at a location such that a second end of the support bracket is positioned adjacent a back of the head of a user wearing the harness;
headgear configured to be worn on the user's head, the headgear comprising a band sized to extend around the back of the head of the user, the headgear coupled to the second end of the support bracket, the support bracket deflectable from a rest position to allow the user to decline the head and provide a counterbalancing force to at least partially support the weight of the head;
a clip configured to be coupled to the band of the headgear, the clip carrying a rail; and
a clevis coupled to the second end of the support bracket to couple the headgear to the second end of the support bracket, the clevis slidable on the rail such that rotation of the head between left and right positions causes the clevis to slide along the rail without deforming the support bracket.

12. A system for supporting a head of a user, comprising:
a harness configured to be worn on a body of a user, the harness including a shoulder harness configured to be worn over or around one or both shoulders of the user; and
a head support comprising:
a support bracket comprising a first end mounted to the harness at a location such that a second end of the support bracket is configured to be positioned adjacent the head of a user wearing the harness;
a rest member coupled to the second end of the support bracket such that the rest member is configured to extend at least partially around the head of the user to contact the user's forehead when the harness is worn;
a rail on the rest member; and
a clevis coupled to the second end of the support bracket to couple the rest member to the support bracket and slidable on the rail such that rotation of the head between left and right positions causes the clevis to slide along the rail; and
an elongate cord coupled between the second end of the support bracket and the clevis, the elongate cord comprising an elastic structure to provide a counterbalancing force,
the head support configured to accommodate the user deflecting the head forward from a rest position while providing the counterbalancing force to at least partially support the weight of the head to prevent or reduce fatigue.

* * * * *